(12) United States Patent
Coles

(10) Patent No.: US 8,592,387 B2
(45) Date of Patent: Nov. 26, 2013

(54) METHODS FOR TREATING OR PREVENTING HEART DAMAGE WITH INTEGRIN-LINKED KINASE (ILK) COMPOSITIONS

(75) Inventor: John G. Coles, Toronto (CA)

(73) Assignee: John G. Coles, Toronto (CA)

( * ) Notice: Subject to any disclaimer, the term of this patent is extended or adjusted under 35 U.S.C. 154(b) by 221 days.

(21) Appl. No.: 12/945,095

(22) Filed: Nov. 12, 2010

(65) Prior Publication Data

US 2011/0117185 A1   May 19, 2011

Related U.S. Application Data

(60) Continuation-in-part of application No. 12/892,065, filed on Sep. 28, 2010, now abandoned, which is a division of application No. 11/915,687, filed as application No. PCT/CA2006/000868 on May 29, 2006, now Pat. No. 7,923,218.

(60) Provisional application No. 60/685,296, filed on May 27, 2005, provisional application No. 61/261,419, filed on Nov. 16, 2009, provisional application No. 61/349,311, filed on May 28, 2010.

(51) Int. Cl.
  *C12N 15/12* (2006.01)
  *A61K 48/00* (2006.01)
  *C12N 15/00* (2006.01)
  *C12Q 1/48* (2006.01)

(52) U.S. Cl.
  USPC ............ 514/44; 435/320.1; 435/15; 435/455; 424/93.2

(58) Field of Classification Search
  None
  See application file for complete search history.

(56) References Cited

FOREIGN PATENT DOCUMENTS

WO    WO2007137414    * 12/2007

OTHER PUBLICATIONS

Lu et al, Integrin-Linked Kinase Expression Is Elevated in Human Cardiac Hypertrophy and Induces Hypertrophy in Transgenic Mice, Circulation. 2006; 114: 2271-2279.*
Guo et al, Protein tolerance to random amino acid change, PNAS, 2004, vol. 101 (25), pp. 9205-9210.*
Lesk et al, Prediction of Protein Function from Protein Sequence and Structure, p. 27 and 28, downloaded Sep. 16, 2007.*
Ding et al. "Increased Expression of Integrin-Linked Kinase Attenuates Left Ventricular Remodeling and Improves Cardiac Function After Myocardial Infarction" *Circulation, Journal of the American Heart Association*, vol. 120, pp. 764-773 (2009).
Dowell et al., "Myocyte and myogenic stem cell transplantation in the heart" *Cardiovascular Research*, vol. 58, pp. 336-350 (2003).
Yau et al., "Enhanced Myocardial Angiogenesis by Gene Transfer with Transplanted Cells" *Circulation, Journal of the American Heart Association*, vol. 104, pp. I-218-I-222 (2001).
Lu et al., "Integin-Linked Kinase Expression is Elevated in Human Cardiac Hypertrophy and Induces Hypertrophy in Transgenic Mice" *Circulation, Journal of the American Heart Association*, vol. 114, pp. 2271-2279 (2006).

* cited by examiner

*Primary Examiner* — Maria Marvich
(74) *Attorney, Agent, or Firm* — Alchemy-Partners, PC

(57) ABSTRACT

The present invention generally provides methods for administering a composition having an ILK-based protein or peptide having a sequence that is at least 90% homologous to wild-type human integrin-linked kinase (ILK) protein for use in treating or administering to cardiac cells in vitro or in vivo. The ILK-based protein or peptide may further have a mutation or substitution at a position corresponding to amino acid position 211 of wild-type human ILK replacing the arginine (R) with an alanine (A). The present invention further provides compositions having polynucleotides encoding such proteins or peptides. Various vectors, delivery reagents and the like are also provided for use in delivering the compositions to cells. The compositions administered to cells in vitro or in vivo according to present methods may be used to treat, prevent, etc., heart failure, ischemic disease, cardiomyopathy, etc.

6 Claims, 22 Drawing Sheets

SEQ ID NO: 1

MDDIFTQCRE GNAVAVRLWL DNTENDLNQG DDHGFSPLHW ACREGRSAVV

EMLIMRGARI NVMNRGDDTP LHLAASHGHR DIVQKLLQYK ADINAVNEHG

NVPLHYACFW GQDQVAEDLV ANGALVSICN KYGEMPVDKA KAPLRELLRE

RAEKMGQNLN RIPYKDTFWK GTTRTRPRNG TLNKHSGIDF KQLNFLTKLN

ENHSGELWKG RWQGNDIVVK VLKVRDWSTR KSRDFNEECP RLRIFSHPNV

LPVLGACQSP PAPHPTLITH WMPYGSLYNV LHEGTNFVVD QSQAVKFALD

MARGMAFLHT LEPLIPRHAL NSRSVMIDED MTARISMADV KFSFQCPGRM

YAPAWVAPEA LQKKPEDTNR RSADMWSFAV LLWELVTREV PFADLSNMEI

GMKVALEGLR PTIPPGISPH VCKLMKICMN EDPAKRPKFD MIVPILEKMQ

Upregulated Genes in R211A Genotype

| Gene Symbol | Gene Name | Fold change | Gene Ontology Biological Process |
|---|---|---|---|
| Ilk | Integrin-linked kinase | 13.3 | integrin-mediated signaling pathway |
| Ifi202b | Interferon-activated gene 202b | 4.1 | protein binding |
| Hspa1b | Hsp70 | 3.4 | response to stress // response to heat negative regulation of caspase activity |
| Hspa1a | Hsp70-3 | 3.1 | response to stress // response to heat |
| Hsph1 | Hsp105 | 2.7 | response to stress //chaperone mediated protein folding requiring cofactor |
| Uap1 | UDP-N-acetylglucosamine pyrophosphorylase 1 | 2.1 | metabolic process |
| Atp1a2 | ATPase, Na+/K+ transporting, alpha 2 polypeptide | 2.1 | ATP biosynthetic process // reduction of cytosolic calcium ion concentration |
| Hsp90aa1 | Hsp90 | 2.0 | response to stress // response to unfolded protein |
| LOC677213 | similar to U2AF homology motif (UHM) kinase 1 | 1.9 | protein amino acid phosphorylation // cell cycle arrest |
| Myh7 | myosin, heavy polypeptide 7, cardiac muscle, beta | 1.8 | response to reactive oxygen species |
| Abhd3 | abhydrolase domain containing 3 | 1.7 | carboxylesterase activity // hydrolase activity |
| Dnaja1 | Hsp40 homolog, subfamily A, member 1 | 1.6 | protein folding // androgen receptor signaling pathway |
| Hspb1 | Hsp25 | 1.6 | response to stress // response to heat |
| Hspa8 | Hsp70 cognate protein | 1.6 | response to stress // chaperone mediated protein folding requiring cofactor |
| Obfc2a | oligonucleotide/oligosaccharide-binding fold containing 2A | 1.6 | nucleic acid binding |

FIG.9-1

| | | | |
|---|---|---|---|
| *P4ha1* | proline 4-hydroxylase, alpha 1 polypeptide | 1.5 | protein metabolic process // collagen fibril organization |
| *Thrsp* | thyoid hormone-responsive protein | 1.5 | protein binding |
| *Clu* | complement lysis inhibitor | 1.5 | anti-apoptosis // response to oxidative stress // positive regulation of cell differentiation // neuron projection morphogenesis |
| *Txnip* | thioredoxin binding protein-2 | 1.5 | response to oxidative stress |
| *Hspa4l* | Hsp70 protein 4-like | 1.5 | response to stress // response to unfolded protein |
| *Ahsa2* | AHA1, activator of heat shock protein ATPase homolog 2 | 1.5 | response to stress |
| *Hspe1* | heat shock protein 1 (chaperonin 10) | 1.5 | protein folding // response to stress |
| *Dnajb1* | Hsp40 homolog, subfamily B, member 1 | 1.5 | response to stress // chaperone mediated protein folding requiring cofactor |

FIG.9-2

| ECHO Variable | ILK_R211A Pos (n=13) | ILK_R211A Neg (n=13) | P-Value | ILK S434D Pos (n=12) | ILK S434D Neg (n=12) | P-Value |
|---|---|---|---|---|---|---|
| Stroke Volume | 27.3 ± 1.3 | 23 ± 1.7 | 0.04 | 19.7 ± 1.3 | 20.2 ± 1.6 | 0.53 |
| Heart Rate | 394 ± 12.5 | 441 ± 28 | 0.02 | 469 ± 8.3 | 454 ± 11.7 | 0.43 |
| Cardiac Output | 8.9 ± 85 | 9.2 ± 1.05 | 0.84 | 9.2 ± 0.63 | 10.2 ± 0.81 | 0.51 |
| End-Diastolic Dimension | 4.9 ± 0.19 | 5.2 ± 0.29 | 0.47 | 5.3 ± 0.23 | 5.0 ± 0.18 | 0.46 |
| End-Systolic Dimension | 4.1 ± 0.24 | 4.5 ± 0.37 | 0.53 | 4.8 ± 0.28 | 4.2 ± 0.22 | 0.33 |
| Fractional Shortening | 16.2 ± 2.2 | 15.6 ± 2.2 | 0.91 | 10.2 ± 1.85 | 15.5 ± 16.5 | 0.3 |
| Pulmonary vein A-Wave | 352 ± 22.5 | 341 ± 41 | 0.85 | 294 ± 25.6 | 319 ± 19 | 0.64 |
| Pulmonary vein D-Wave | 231 ± 72 | 271 ± 87 | 0.39 | 145 ± 38.2 | 194 ± 48 | 0.27 |

FIG. 10

| ECHO Variable | ILK_R211A Pos (n=13) | ILK_R211A Neg (n=13) | P-Value | ILK S434D Pos (n=12) | ILK S434D Neg (n=12) | P-Value |
|---|---|---|---|---|---|---|
| Infarct | 5.4 ± 0.22 | 7.2 ± 0.34 | 0.04 | 6.5 ± 0.31 | 7.6 ± 0.27 | 0.12 |
| Viable Myocardium Anterior Wall | 5.7 ± 0.42 | 4.25 ± 0.3 | 0.001 | 5.1 ± 0.25 | 4.2 ± 0.21 | 0.05 |

FIG. 11

METHODS FOR TREATING OR PREVENTING HEART DAMAGE WITH INTEGRIN-LINKED KINASE (ILK) COMPOSITIONS

CROSS-REFERENCE TO RELATED APPLICATIONS

This application is a continuation-in-part application of U.S. patent application Ser. No. 12/892,065, filed Sep. 28, 2010, now abandoned, which is a divisional application of U.S. patent application Ser. No. 11/915,687, filed Nov. 27, 2007, now U.S. Pat. No. 7,923,218 which is a national stage entry of PCT/CA06/00868, filed May 29, 2006, which further claims the benefit of priority to U.S. Provisional Patent App. No. 60/685,269, filed May 27, 2005. This application claims the benefit of priority to U.S. Provisional Patent App. No. 61/349,311, filed May 28, 2010. This application also claims the benefit of priority to U.S. Provisional Patent App. No. 61/261,419, filed Nov. 16, 2009. The entire contents and disclosures of each of the above patent applications are hereby incorporated by reference.

SEQUENCE LISTING

The instant application contains a Sequence Listing which has been submitted in ASCII format via EFS-Web and is hereby incorporated by reference in its entirety. Said ASCII copy, created on Dec. 17, 2010, is named 42145402.txt and is 10,142 bytes in size.

BACKGROUND

1. Field of the Invention

The present invention relates generally to the field of treatments for the prevention and/or healing of cardiac tissue against heart failure or ischemic conditions and the manipulation of cardiac cells in vivo or in vitro.

2. Related Art

Heart failure (HF) is a progressive condition in which the heart can no longer pump enough blood to the rest of the body. There can be many causes of heart failure in individuals. Common causes of heart failure may include myocardial infarction (heart attacks) and other forms of ischemic heart disease, hypertension, valvular heart disease, and cardiomyopathy.

For example, dilated cardiomyopathy (DCM) is a heterogenous group of inherited and acquired disease characterized by cardiac dilation and reduced systolic function, usually evident in the second or third decade of life. Adult and childhood forms of DCM may be primary or idiopathic (50-70%), or secondary to sarcomeric gene mutations. DCM is an important and common cause of acute and chronic heart failure (HF), but also exhibits many pathophysiological features, such as loss of ventricular mass and replacement fibrosis, typical of HF of diverse causation, including end-stage ischemic cardiomyopathy. DCM is characterized by enlargement of the cardiac chambers, decreased myocardial contractility and unspecific histopathological findings, such as myocyte loss, increased apoptosis and interstitial fibrosis. Mutations associated with DCM have been identified in genes including β-MHC, cMyBPC, cardiac actin, cTnT, cTnI, and cTnC among others.

Doxorubicin is an effective and frequently used chemotherapeutic agent for various malignancies. The major limitation of this class of highly effective chemotherapeutic drug is its dose-dependent cardiotoxicity, resulting in the death of cardiomyocytes which often leads to irreversible myocardial dysfunction. Doxorubicin-induced cardiomyopathy (DOXO-DCM) is a specific and lethal complication of chronic doxorubicin therapy for which there is no treatment other than transplantation. Although DOXO-DCM is a specific form of DCM, it shares many unifying pathophysiological features with DCM of diverse causation, including the findings of extensive fibrosis, fibroblast proliferation, and myocytic and myofibril loss, in association with dilated phenotype and profound biventricular dysfunction. Purported mechanisms of DOXO DCM include excessive oxidative stress, myocyte apoptotic loss, and down-regulation of contractile genes such as myosin light and heavy chains, troponin-I, and desmin proteins. Although anti-oxidants and vincristine have demonstrated various degrees of efficacy in murine models of DOXO cardiotoxicity, there are currently no non-toxic, clinically viable drugs available for this indication, and clinical evidence of congestive heart failure usually denotes a lethal outcome without transplantation.

Childhood idiopathic DCM is a rare but highly debilitating disease of multiple causes with profound morbidity and mortality. The 1- and 5-year rates for death or transplantation for children with DCM based on National Heart, Lung, and Blood Institute's Pediatric Cardiomyopathy Registry are 39% and 53%, respectively, illustrating the inadequacy of current medical therapy. In 40% of children with symptomatic DCM, medical therapy fails within 2 years of diagnosis. The treatment for advanced heart failure resulting from childhood (and adult) DCM may involve escalating inotropic therapy, ventilation, and ultimately, deployment of ventricular assist devices (VADs) as a bridge to transplantation.

Currently there is no mechanism-based treatment available for Heart Failure, irrespective of etiology so that the prognosis of patients with chronic HF remains poor. New advances in the treatment of patients with DCM in the last decade rely on indirect methods to improve cardiac function, such as the combined use of angiotensin converting enzyme (ACE) inhibitors, angiotensin II receptor (AR) antagonists, β-blockers, aldosterone antagonists and diuretics. Consequently, HF related mortality remains elevated, approaching 50% at 5 years in symptomatic patients, and constitutes, by disease category, a huge economic health care burden worldwide. Non-pharmacologic therapies, such as heart transplantation and the use of implantable assist devices, are considered only in the later stages of the disease, and access to such therapies is restricted to a fraction of patients who need them.

Thus, there continues to be an urgent need for the development of novel and specific anti-heart failure treatments for advanced heart failure of diversified etiologies.

SUMMARY

According to a first broad aspect of the present invention, a method is provided comprising administering a composition comprising a protein or peptide having a sequence that is at least 90% homologous to human ILK protein (SEQ ID NO: 1), or a functional fragment thereof, to one or more cells, wherein the one or more cells comprise one or more cardiac cells or one or more cells capable of differentiation into cardiac cells. According to some embodiments, the protein or peptide further comprises an amino acid substitution at a position corresponding to amino acid residue 211 of human ILK (SEQ ID NO: 1) replacing arginine (R) with alanine (A).

According to a second broad aspect of the present invention, a method is provided comprising administering a composition comprising a polynucleotide encoding a protein or peptide having a sequence that is at least 90% homologous to human ILK protein (SEQ ID NO: 1), or a functional fragment thereof, to one or more cells, wherein the one or more cells comprise one or more cardiac cells or one or more cells capable of differentiation into cardiac cells. According to some embodiments, the polynucleotide encodes a protein or peptide having an amino acid substitution at a position corresponding to amino acid residue 211 of human ILK (SEQ ID NO: 1) replacing arginine (R) with alanine (A).

According to a third broad aspect of the present invention, a method is provided comprising administering one or more cells having an exogenous protein or peptide having a sequence that is at least 90% homologous to human ILK protein (SEQ ID NO: 1), or a functional fragment thereof, or an exogenous polynucleotide encoding the protein or peptide or functional fragment thereof, to the heart of an individual, wherein the one or more cells comprise one or more cardiac cells or one or more cells capable of differentiation into cardiac cells.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 1 is the full-length protein sequence for wild-type human integrin-linked kinase (ILK) displaying the arginine (R) at amino acid position 211, which is substituted with alanine (A) in the ILK_R211A mutant protein, in bold and underlined.

FIG. 9 is a table of upregulated genes in ILK_R211A expressing cells showing robust induction of heat-shock protein transcriptional response.

FIG. 10 is a table showing echocardiographic assessment of cardiac function (mean±SEM) performed in transgenic mice harboring ILK activation-resistant (ILK$^{R211A}$) and activated (ILK$^{S343D}$) mutations and littermate controls at 28 days post-LAD ligation. P values were calculated using ANOVA. Pos, genotype-positive; Neg, genotype-negative, littermate controls.

FIG. 11 is a table showing echocardiographic assessment of infarct size performed (mean±SEM) in transgenic mice conveying ILK$^{R211A}$ and ILK$^{S343D}$ mutations and littermate controls at 28 days post-LAD ligation with infarct size taken to be the length of myocardium which was akinetic in the parasternal long axis view. P values were calculated using ANOVA. Pos, genotype-positive; Neg, genotype-negative, littermate controls.

DETAILED DESCRIPTION OF THE PREFERRED EMBODIMENTS

Definitions

Figure 2A:
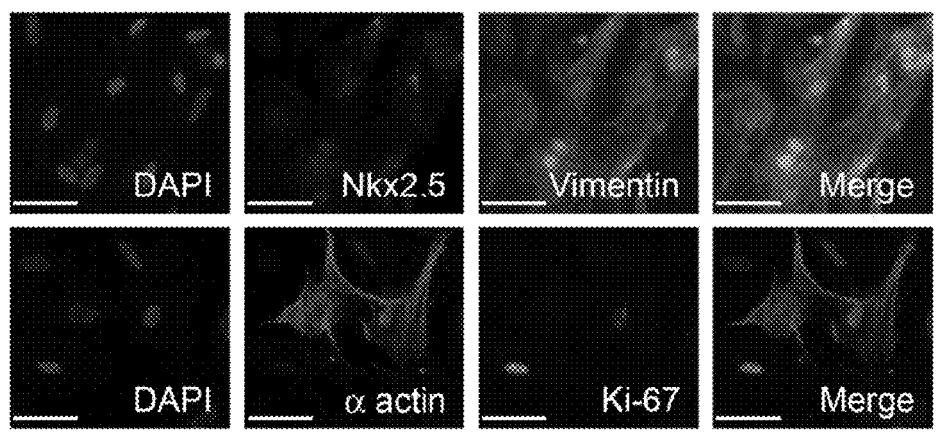
FIG. 2A is a set of images of immune-stained cells isolated from human fetal myocardium. Cells freshly isolated from 22 weeks-old human fetal myocardium were cultured for 2 days and then double immune-stained with anti-nkx2.5 (red) and anti-vimentin (green) (top panel) or with anti-α-actin (red) and anti-ki-67 (green) (bottom panel) antibodies to determine the percentage of the cells with cardiomyocyte or fibroblast phenotype. Nuclei were marked with DAPI staining (blue). Scale bar 30 μm.

Where the definition of terms departs from the commonly used meaning of the term, applicant intends to utilize the definitions provided below, unless specifically indicated.

For purposes of the present invention, the term "individual" refers to a mammalian organism, but may preferably refer to a human individual or person.

For purposes of the present invention, the term "cardiac cell" refers to any cell at any stage of cardiac development or within the cardiac lineage of cells, any cardiac cell type, any cell forming part of the heart of an individual, or any cell capable of differentiation into a cardiac cell or cardiac cell type.

For purposes of the present invention, the term "cardiac cell type" refers to a cell displaying features, such as cell surface or epigenetic markers, characteristic of cardiac cells.

For purposes of the present invention, the term "exogenous" refers to a molecule originating outside a cell, which may be engineered and/or introduced artificially into a cell.

For purposes of the present invention, the term "polynucleotide" refers to any DNA or RNA molecule that encodes a protein or peptide, such as an ILK-based protein or peptide.

For purposes of the present invention, the term "corresponding" refers to an amino acid sequence or position of a protein or peptide corresponding to another amino acid sequence or position of another protein or peptide or reference sequence according to standard criteria in the art, such as by matching sequence alignment, functional domains, etc.

For purposes of the present invention, the term "homologous" refers to the degree of identity between two or more proteins and/or peptides or the degree of identity between a protein and a reference sequence over the corresponding length of the shorter protein, peptide or reference sequence between them. For example, a protein having at least 90% homology to another protein or sequence will have at least 90% of its amino acids that are identical at corresponding positions over the length of overlap between them.

For purposes of the present invention, the term "ILK-based" refers to any protein or peptide having a high degree of sequence homology to human ILK (SEQ ID NO: 1) to be recognizable as being related functionally to human ILK.

For purposes of the present invention, the terms "encode" or "encoding" refer to the ability or characteristic of a polynucleotide be transcribed and translated into a reference protein or peptide encoded thereby.

For purposes of the present invention, the term "functional fragment" refers to a fragment of a protein that retains one or more functions or interactions of the wild-type or full-length protein even if one or more function(s), functional domain(s) or interaction(s) of the wild-type or full-length protein is missing. For example, a functional fragment of a protein having a kinase domain, such as ILK, may be any fragment of that protein that retains kinase function.

Description

Integrin-linked kinase (ILK) is a multidomain integrin adaptor protein that possesses widely conserved structural and signal transduction functions. ILK binds to cytoplasmic domains of β1-, β2-, and β3-integrin subunits and nucleates a supramolecular complex at the site of focal adhesions that connects to the actin cytoskeleton, thereby linking the extracellular matrix to the cytoskeleton in a manner essential for bidirectional force transduction. See, e.g., Legate K R, et al. "Mechanisms that regulate adaptor binding to beta-integrin cytoplasmic tails," *J Cell Sci,* 122(2):187-198 (2009), the entire contents and disclosure of which are hereby incorporated by reference. Adaptor complexes centered around ILK comprise a signaling platform that, in response to distinct signal inputs from integrins and growth factor receptor tyrosine kinases, activates signaling pathways regulating growth, survival, cell cycle progression, epithelial-mesenchymal transition, and cellular differentiation. See, e.g., Legate K R et al., "Genetic and cell biological analysis of integrin outside-in signaling," *Genes Dev,* 23(4):397-418 (2009); and Hannigan G et al., "Integrin-linked kinase: a cancer therapeutic target unique among its ILK," *Nat Rev Cancer,* 5(1):51-63 (2005), the entire contents and disclosure of which are hereby incorporated by reference.

ILK is a multidomain integrin adaptor protein that possesses widely conserved structural and signal transduction functions. McDonald P C et al., "Integrin-linked kinase—essential roles in physiology and cancer biology," *J Cell Sci* 121(Pt 19):3121-3132 (2008), the entire contents and disclosure of which are hereby incorporated by reference. In the heart, ILK has been shown to subserve dual function as a mechanoreceptor and as a nodal regulator of adaptive, pro-hypertrophic signaling. See, e.g., Lu H et al., "Integrin-linked kinase expression is elevated in human cardiac hypertrophy and induces hypertrophy in transgenic mice," *Circulation,* 114(21):2271-2279 (2006); and Hannigan G E et al., "Integrin-linked kinase at the heart of cardiac contractility, repair, and disease," *Circ Res,* 100(10):1408-1414 (2007), the entire contents and disclosure of which are hereby incorporated by reference. ILK-deficient mice die early during embryonic development owing to defects in epiblast polarization with an abnormal distribution of F-actin. See, e.g., Sakai T et al., "Integrin-linked kinase (ILK) is required for polarizing the epiblast, cell adhesion, and controlling actin accumulation," *Genes Dev,* 17(7):926-940 (2003), the entire contents and disclosure of which are hereby incorporated by reference. Specific localization of ILK to costameric and Z-disc structures could imply a functional role in the integration of cardiac mechanoreception and contractility. See, e.g., Samarel A M, "Costameres, focal adhesions, and cardiomyocyte mechanotransduction. *Am J Physiol Heart Circ Physiol,* 289(6): H2291-2301 (2005), the entire contents and disclosure of which are hereby incorporated by reference.

Disruption of ILK kinase activity results in a heart failure phenotype in zebrafish that is dependent upon ILK-mediated vascular endothelial growth factor signaling (VEGF), and conditional ILK deletion in the mouse heart causes spontaneous dilated cardiomyopathy (DCM) and sudden death at 6 to 12 weeks of age, suggesting an important and distinct role of ILK during vertebrate cardiac morphogenesis. See, e.g., Bendig G et al., "Integrin-linked kinase, a novel component of the cardiac mechanical stretch sensor, controls contractility in the zebrafish heart," *Genes Dev,* 20(17):2361-2372 (2006); and White D E et al., "Targeted ablation of ILK from the murine heart results in dilated cardiomyopathy and spontaneous heart failure," *Genes Dev,* 20(17):2355-2360 (2006), the entire contents and disclosure of which are hereby incorporated by reference.

ILK activation by growth factor stimulation is normally regulated in a PI3K-dependent manner involving activation of ILK by phosphatidylinositol (3,4,5)-trisphosphate (PIP3), thought to involve interaction with the central pleckstrin homology (PH)-like domain of ILK. See, e.g., Delcommenne M et al., "Phosphoinositide-3-OH kinase-dependent regulation of glycogen synthase kinase 3 and protein kinase B/AKT by the integrin-linked kinase," PNAS USA, 95(19):11211-11216 (1998), the entire contents and disclosure of which are hereby incorporated by reference. Canonical ILK signaling induces downstream phosphorylation of Akt/PKB on Ser473 and glycogen synthase-3β (GSK-3β) on Ser9, providing a molecular basis for its prosurvival, prohypertrophic effects. See, e.g., Lu H et al., (2006), supra; Hannigan G E et al., (2007), supra; and White D E et al., (2006), supra. Interestingly, the ILK gene contains hypoxia responsive elements and upon exposure to hypoxia, activates endothelial cell (EC) expression of hypoxia inducible factor 1-α (HIF-1α) and VEGF. In turn, receptor tyrosine kinase activation by VEGF stimulates HIF-1α in an amplification loop involving PI3K and ILK activation. See, e.g., Abboud E R et al., "Integrin-linked kinase: a hypoxia-induced anti-apoptotic factor exploited by cancer cells," Int J Oncol, 30(1):113-122 (2007), the entire contents and disclosure of which are hereby incorporated by reference. ILK has been shown to be an upstream regulator of the EC hypoxic stress response that controls the recruitment of endothelial progenitor cells to ischemic tissue. See, e.g., Lee S P et al., "Integrin-linked kinase, a hypoxia-responsive molecule, controls postnatal vasculogenesis by recruitment of endothelial progenitor cells to ischemic tissue," Circulation, 114(2):150-159 (2006), the entire contents and disclosure of which are hereby incorporated by reference.

ILK has also been shown to regulate the Wnt signaling pathway to stimulate β-catenin/T cell factor (Tcf) transcriptional activity through negative regulation of GSK-3β. See, e.g., Hannigan G et al., (2005), supra. Chemical inhibitors of GSK-3β and activation of β-catenin promote expansion of embryonic and postnatal Islet-1 (Isl1) cardiac progenitor cells. See, e.g., Qyang Y et al., "The renewal and differentiation of Isl1+ cardiovascular progenitors are controlled by a Wnt/beta-catenin pathway," Cell Stem Cell 1(2):165-179 (2007), the entire contents and disclosure of which are hereby incorporated by reference. Tcf3 acts as a cell-intrinsic inhibitor of pluripotent cell self-renewal through repressive binding to the Oct4 promoter, and ILK-mediated activation of the Tcf3 transcriptional complex may be predicted to favor cellular differentiation. See, e.g., Yi F et al., "Tcf3 functions as a steady-state limiter of transcriptional programs of mouse embryonic stem cell self-renewal," Stem Cells, 26(8):1951-1960 (2008); and Tam W L et al., "T-cell factor 3 regulates embryonic stem cell pluripotency and self-renewal by the transcriptional control of multiple lineage pathways," Stem Cells, 26(8):2019-2031 (2008), the entire contents and disclosure of which are hereby incorporated by reference. Activation of the Wnt/β-catenin pathway promotes cardiogenesis in early phase mouse ES cells. See, e.g., Naito A T et al., "Developmental stage-specific biphasic roles of Wnt/beta-catenin signaling in cardiomyogenesis and hematopoiesis," Proc Natl Acad Sci USA, 103(52):19812-19817 (2006), the entire contents and disclosure of which are hereby incorporated by reference.

It has been shown that ILK overexpression in transgenic mice leads to a "beneficial" hypertrophy with preserved cardiac function. ILK transgenic mice further exhibit preserved heart wall thickness with a reduction in scar area following LAD ligation. In separate experiments, it has been demonstrated that human fetal cardiomyocytes (HFCMs) infected with an adenoviral vector for expressing ILK formed primary spheres of c-kit-positive cardiac stem cells at a much higher frequency in culture, which were further capable of generating secondary spheres after their dissociation. These cells were further capable of subsequent multi-lineage differentiation demonstrating their ability not only for self-renewal but also for differentiation into multiple cardiac cell types. See, e.g., U.S. patent application Ser. No. 12/892,065.

It is further shown herein that ILK expression is cardioprotective and promotes cardiomyogenesis of increased numbers of cardioblasts. It is shown that expression of a mutant ILK_R211A (see below) in transgenic mice increases hsp70/hsc70 expression and binding to the mutant ILK_R211A leading to its increased expression and signaling. Expression of ILK, but particularly the mutant ILK_R211A protein, reduced infarct size and improved stroke volume (increased) and heart rate (decreased) following LAD ligation in Tg mice. ILK expression is further shown to upregulate expression of sarcoplasmic endoplasmic reticulum ATPase, isoform 2a (SERCA2), and the down-regulation of SERCA2 is associated with impaired $Ca^{2+}$ sequestration, a hallmark of reduced contractility and diastolic dysfunction characteristic of advanced HF. Therefore, the increased level of SERCA2 observed in ILK expressing cardiac cells is believed to provide additional cardioprotection.

Not only is ILK expression cardioprotective, ILK overexpression leads to increased numbers of cells undergoing cardiomyogenesis. ILK overexpressing cells give rise to a greater number of nkx2.5-positive aggregates of primary cardioblast cells in culture, presumably derived from mesodermal precursors. As a result of increased Wnt signaling through β-cat, these ILK-overexpressing cells further increase expression of Isl-1 and differentiate into cardiomyoblasts to a larger extent. These cardiomyogenic effects of ILK overexpression were observed to an even greater extent in ILK_R211A overexpresing cells.

According to a broad aspect of the present invention, a method of treating cardiac cells or cells capable of differentiation into cardiac cells (including cardiac precursor, progenitor or stem cells) or heart tissue in vivo or in vitro with a composition comprising a mammalian integrin-linked kinase (ILK) protein or peptide, such as a composition comprising a protein or peptide having a sequence that is at least 90% or at least 95% homologous to human ILK protein (FIG. 1; SEQ ID NO: 1) or a functional fragment thereof, or a composition comprising a polynucleotide molecule encoding any such ILK protein or functional fragment thereof, is provided. Such a protein or peptide or functional fragment thereof may have any length but may be, for example, at least 50, at least 100, at least 150, at least 200, at least 250, at least 300, at least 350, or at least 400 amino acids in length according to some embodiments. Such a treatment method may be used to protect, prevent, ameliorate, etc., against heart damage during an acute myocardial infarction or as a result of heart failure or ischemic syndromes in an individual, such as a human individual. Such a treatment method may also be used to promote healing, remodeling and/or beneficial hypertrophy of heart tissue following either acute or chronic heart damage in an individual, such as a human individual.

Oncogenesis represents a biological and regulatory risk inherent in all cardio- and neural-cytoprotective strategies, which has not been adequately addressed by the regenerative medicine drug target development industry. ILK has been variously implicated as an oncogene and as a tumor suppressor. See, e.g., Hannigan G et al., "Integrin-linked kinase: a cancer therapeutic target unique among its ILK," Nat Rev Cancer 5(1):51-63 (2005); Chen P et al., "Suppression of malignant growth of human breast cancer cells by ectopic expression of integrin-linked kinase," Int J Cancer 111(6):881-891 (2004); and Hess F et al., "Integrin-linked kinase interacts with caspase-9 and -8 in an adhesion-dependent manner for promoting radiation-induced apoptosis in human leukemia cells," *Oncogene* 26(10):1372-1384 (2007). Studies have suggested that a region of LOH lies over the ILK locus in numerous cell types, including ERMS, breast carcinoma, and non-small cell lung carcinoma. See, e.g., Karnik P et al., "Two distinct tumor suppressor loci within chromosome 11p15 implicated in breast cancer progression and metastasis," *Hum Mol Genet* 7(5):895-903 (1998). The implementation of ILK as a therapeutic strategy is limited by the general therapeutic paradigm that cytoprotective and pro-survival strategies are inherently associated with potential onogenic risks. This potential for oncogenicity creates a challenge and risk in altering ILK function in the treatment of disease.

As explained above, ILK activation by growth factor stimulation is normally regulated in a phosphatidylinositol 3-Kinase (PI3K)-dependent manner involving activation of ILK by phosphatidylinositol (3,4,5)-trisphosphate (PIP3), thought to involve interaction with the central pleckstrin homology (PH)-like domain of ILK. A mutant of ILK having a point mutation in its PH domain (ILK_R211A) impairs membrane PIP3 binding and renders it resistant to receptor-mediated activation, thus neutralizing the potentially oncogenic properties of the native ILK molecule. See, e.g., Persad S et al., "Regulation of protein kinase B/Akt-serine 473 phosphorylation by integrin-linked kinase: critical roles for kinase activity and amino acids arginine 211 and serine 343," *J Biol Chem* 276(29):27462-27469 (2001). Indeed, the ILK_R211A mutant has been shown to be kinase-inert and phenotypically null in several cancer cell lines. See, e.g., Durbin A D et al., "JNK1 determines the oncogenic or tumor-suppressive activity of the integrin-linked kinase in human rhabdomyosarcoma," *J Clin Invest*, 119(6):1558-1570 (2009).

Therefore, it is proposed that the ILK_R211A mutant protein may be therapeutically advantageous if it were to maintain its beneficial cardioprotective and cardiomyogenic properties while avoiding the oncogenic risk associated with activation and growth factor signaling through wild-type ILK. It is shown herein that ILK_R211A is potently cardioprotective through several mechanisms, including (1) phosphorylation and downregulation of the key cytoprotective target glycogen synthase-3β (GSK-3β) (see, e.g., Walsh M D X et al., "Integrin linked kinase (ILK) is cardioprotective against ischemia," Presented at 2009 American Heart Association Congress), (2) induction of cardiomyogenesis through activation of the ILK-regulated Wnt signaling target, β-catenin (see, e.g., Traister A H A et al., "Integrin-linked kinase induces cardiomyogenesis in human fetal heart," Presented at 2009 American Heart Association Congress), and (3) through induction of adaptive hypertrophy in the human heart.

Surprisingly, it is further shown herein that ILK_R211A protein expression is more cardioprotective than wild type ILK (and a constitutively active form of ILK (ILK_S343D)) as evident in mouse models of MI and by the capacity of ILK_R211A to promote new cardiomyogenesis in human cardiac cells derived from DCM patients. This superior effect of ILK_R211A protein is apparently due in part to its induction of a heat-shock response and interaction with Hsp70 cognate protein (Hsc 70) likely resulting from its misfolding, which serves to enhance its expression level and cell autonomous signaling function. In addition, it is further shown that ILK upregulates a key heart failure target, sarcoplasmic endoplasmic reticulum ATPase, isoform 2a (human orthologue, SERCA2) (see Examples below). Moreover, not only is the ILK_R211A mutant protein shown to be more cardioprotective than the wild-type protein, ILK_R211A is further predicted to be cardio-selective and have off-target "inertness" since it is non-responsive to growth factor-mediated activation in non-cardiac tissues. The capacity of this molecule to signal in a cardiomyocte-restricted manner and not through exogenous growth signals conveys cardioselective potency.

According to embodiments of the present invention, a method of treating cardiac cells or cells capable of differentiating into cardiac cells (including cardiac precursor, progenitor or stem cells) or heart tissue in vivo or in vitro with a composition comprising a mutant mammalian integrin-linked kinase (ILK) protein or peptide, such as a composition comprising a protein or peptide having a sequence that is at least 90% or at least 95% homologous to human ILK protein (FIG. 1; SEQ ID NO: 1) or a functional fragment thereof, and having a mutation at a position corresponding to amino acid residue 211 of wild-type human ILK (numbered from the N-terminus of the full length protein sequence as shown in FIG. 1) replacing the arginine (R) at such position with another amino acid, such as alanine (A), or a functional fragment thereof, or a composition comprising a polynucleotide molecule encoding any such mutant ILK protein or functional fragment thereof, is provided. According to some embodiments, such a composition may comprise a human ILK_R211A protein (SEQ ID NO: 2) or a functional fragment thereof, or a polynucleotide molecule encoding the ILK_R211A protein or a functional fragment thereof. Such a treatment method may be used to protect, prevent, ameliorate, etc., against heart damage during or following an acute myocardial infarction or as a result of heart failure, ischemic conditions or syndromes, cardiomyopathies (familial, idiopathic, primary or secondary to cardiotoxic drugs, such as doxorubicin), and/or post-surgical cardiac dysfunction for congenital or acquired heart disease, in an individual, such as a human individual. Such a treatment method may also be used to promote healing, remodeling and/or beneficial hypertrophy of heart tissue following either acute or chronic heart damage or ischemic conditions in an individual, such as a human individual.

Since ILK_R211A mutant protein has been shown to be resistant to receptor-mediated activation as a result of a point mutation in its PH domain, this molecule is proposed as a first-in-class cytoprotective and potently cardioselective molecule to possess null off-target, oncogenic effects. Accordingly, it is presently proposed that other mutants or deletions that may be used in compositions according to method embodiments of the present invention may be designed to have similar functional properties and beneficial effects similar to the ILK_R211A mutant. These additional mutants and deletions of ILK would be expected to have the capacity to promote cytoprotective signaling without possessing the susceptibility to excessive activation resulting, for example, from oncogenic mutations in other signaling pathways such as occurs in the PI3K pathway in many cancers. For example, since the ILK_R211A mutant has a mutation in the pleckstrin homology (PH)-like domain of ILK, it is expected and proposed that other mutations or deletions of variable length within the PH domain of the ILK protein (defined as corresponding to amino acids 180 through 212 of the human ILK protein sequence shown in SEQ ID NO: 1), or functional fragment thereof, may have similar properties as the ILK_R211A mutant protein. For ILK mutant proteins having one or more deletions within the PH domain of ILK, the position of such a deletion(s) may theoretically delete any portion of the PH domain and may vary in terms of the length of the deletion from one amino acid within the PH domain up to the entire length of the PH domain. In addition, other point mutations or substitutions within the PH domain of ILK may also be used.

According to some embodiments, therefore, a method is provided of treating cardiac cells or cells capable of differentiating into cardiac cells (including cardiac precursor, progenitor or stem cells) or heart tissue in vivo or in vitro with a composition comprising a mutant mammalian integrin-linked kinase (ILK) protein or peptide, such as a composition comprising a protein or peptide having a sequence that is at least 90% or at least 95% homologous to human ILK protein (FIG. 1; SEQ ID NO: 1) or a functional fragment thereof, that has a mutation or a deletion of variable length within or including a portion of the protein or peptide corresponding to the PH domain of the human ILK protein (defined as amino acids 180 through 212 of the human ILK protein sequence shown in SEQ ID NO: 1), or a polynucleotide encoding such a protein or peptide or a functional fragment thereof.

According to embodiments of the present invention, a method of treating cardiac cells (including cardiac precursor, progenitor or stem cells) or heart tissue in vivo or in vitro with a composition comprising ILK, ILK_R211A or other mutant ILK protein having a mutation or deletion in its PH domain is provided, which may be used as a therapeutic agent to protect, prevent, ameliorate, etc., against heart damage in an individual during or resulting from acute myocardial infarction or ischemic syndromes. Such protective effects or outcomes of the present method embodiments may include, for example: (1) induction of hypertrophy in the myocardium, such as in the remote myocardium or at the border of an infarct area, and/or salvage of vulnerable, border zone myocytes; (2) upregulation of cytoprotective signaling by phosphorylation of established ILK targets PKB/Akt (activation) and GSK-3β (inactivation); (4) upregulation of heat-shock proteins (Hsps) and/or SERCA2; (5) increased cardiac contractility and/or diastolic heart function; (6) recruitment of increased numbers of Isl-1 or GATA4-expressing cells and/or nkx2.5 positive cardioblasts from mesodermal precursors; and/or (7) stimulation of new cardiomyogenesis of precursor cells resident or mobilized to the heart following injury.

According to embodiments of the present invention, one or more outcomes (in addition to those above) may be used to measure a therapeutic or desired effect following administration of an ILK-based composition according to present methods, such as: (1) biopsy-proven cardiomyogenesis in an individual; (2) activation/deactivation of ILK signaling by increased expression level or phosphorylation of ILK targets including GSK-3β, Akt/PKB, SERCA2, and/or Hsp70/Hsc70; (3) increased interaction or binding of ILK to any one or more of these targets; (4) measurement of cardiac function or output according to standard techniques, such as by echocardiography or measurement of infarct area, stroke volume, contractility, heart rate, etc.; and (5) measurement of the apoptotic threshold (e.g., ATP levels, caspase 3 or 7 activity, trypan blue assay, etc.). Basically, any method, technique, assay, etc., known in the art or described herein may be used to ascertain the effect or outcome of a method embodiment of the present invention. See, e.g., Lu, H et al., (2006), supra; Coles J G et al., "Cardioprotective stress response in the human fetal heart," *J Thorac Cardiovasc Surg* 129(5):1128-1136 (2005); Riazi A M et al., "NKX2-5 regulates the expression of beta-catenin and GATA4 in ventricular myocytes," *PLoS ONE* 4(5):e5698 (2009); and Yamabi H et al., "Overexpression of integrin-linked kinase induces cardiac stem cell expansion," *J Thorac Cardiovasc Surg* 132(6):1272-1279 (2006), the entire contents and disclosure of which is hereby incorporated by reference.

Sarcoplasmic reticulum (SR) function is regulated predominantly by proteins controlling $Ca^{2+}$ cycling, principally reflected in the ratio of SERCA2/phosphlamban (PLB) (see below). Accordingly, measurement of the SERCA2/PLB ratio in cardiac cells may also be used to measure outcome or effect of following, or in response to, treatment or administration of an ILK-based composition according to method embodiments of the present invention with an increased SERCA2/PLB ratio indicating improvement. In addition, measurement of $Ca^{2+}$ dynamics, current or flow ($Ca^{2+}$ transients, SR $Ca^{2+}$ load, $Ca^{2+}$ content during wave development, L-type $Ca^{2+}$ current) may also be used to determine the effect or outcome of method embodiments of the present invention, such as by $Ca^{2+}$ confocal fluorescent imaging in Fluo-4AM-loaded in cells, by patch clamping, etc.

Embodiments of the present invention have the potential advantage of time compressed target development since the methods use the ILK compositions identified herein "as is" in gene therapy or other strategies, thus circumventing the need for additional screens and lead optimization typical for small-molecule drugs. Although cellular-based strategies of the present invention are contemplated and described, method embodiments of the present invention based on gene therapy strategies may be used to enhance the proven endogenous regenerative capacity of the target heart organ and cardiac cells.

According to some method embodiments of the present invention, a composition comprising a polynucleotide encoding a mammalian integrin-linked kinase (ILK) protein or peptide having a sequence that is at least 90% or at least 95% homologous to human ILK protein (FIG. 1; SEQ ID NO: 1) or a functional fragment thereof may be administered to a mammalian or human cell in vitro or in vivo, such as a cardiac stem cell, mesodermal cell, mesenchymal cell, primary cultured cardiac cell, cardioblast, cardiomyocyte, or any other cardiac cell including a heart precursor or progenitor cell, a heart smooth muscle or endothelial cell, or to an induced pluripotent stem (iPS) cell, to express the encoded ILK protein in the cell. Such a cell may generally be any cell or cell type capable of differentiation into a cardiac cell or cardiac cell type, which may normally be found in the heart of a mammal, such as a human.

According to some embodiments, a composition administered to such a cell in vitro or in vivo may be a composition comprising a polynucleotide encoding a mutant mammalian integrin-linked kinase (ILK) protein or peptide, such as a composition comprising a polynucleotide encoding a protein or peptide having a sequence that is at least 90% or at least 95% homologous to human ILK protein (FIG. 1; SEQ ID NO: 1) or a functional fragment thereof, wherein the ILK protein or peptide encoded by the polynucleotide has a mutation or substitution at a position corresponding to amino acid residue 211 of wild-type human ILK (numbered from the N-terminus of the full length protein sequence as shown in FIG. 1) that replaces the arginine (R) at such position with another amino acid, such as alanine (A). For example, the composition may comprise a polynucleotide encoding human ILK_R211A protein (SEQ ID NO: 2), or a functional fragment thereof.

Such a polynucleotide of the present invention according to some embodiments may further include any suitable promoter or enhancer sequence element(s) to drive expression of an ILK protein or peptide encoded by the polynucleotide in the cell. Such a promoter according to embodiments of the present invention may also be any promoter that limits or targets expression of the wild-type or mutant ILK protein in cardiac cells or tissue, such as a promoter of the cardiac specific α-myosin heavy chain.

According to embodiments of the present invention, the composition comprising a polynucleotide encoding a protein or peptide having a sequence that is at least 90% or at least 95% homologous to human ILK protein (FIG. 1; SEQ ID NO: 1) or a functional fragment thereof, with or without the corresponding R211A mutation or substitution, may be administered to the cell either transiently or stably according to any "gene therapy" technique or approach known or available in the art. Gene therapy techniques or approaches according to embodiments of the present invention may include any known method or technique in the art for administering a polynucleotide or nucleic acid into the interior of a cell either in vitro or in vivo. Such gene therapy techniques or approaches according to some embodiments may administer either a naked polynucleotide or DNA molecule or a polynucleotide or DNA molecule as part of any suitable plasmid or vector known in the art for delivery into an animal or mammalian cell.

Suitable vectors for carrying the polynucleotide of present embodiments that may be used according to known methods may include recombinant viruses, such as retroviruses, adenoviruses, adeno-associated virus (AAV), or any other virus known for its use in gene therapy in mammalian or human cells, or any other integratable or transfection vector in mammalian or human cells. A polynucleotide used as part of method embodiments of the present invention may be incorporated into any of these vectors according to known techniques. See, e.g., U.S. Pat. Nos. 7,820,438; 7,790,683; and 7,785,599, the relevant contents and disclosure of which are hereby incorporated by reference. For further discussion of methods for gene therapy into cardiac cells or cardiomyocytes, see, e.g., U.S. patent application Ser. No. 12/391,257 and U.S. Pat. No. 7,399,750, the relevant contents and disclosure of which are hereby incorporated by reference. According to some embodiments, administration of the viral vector may be tailored to preferentially target cardiac cells or tissue. See, e.g., U.S. patent application Ser. No. 12/447,558, the relevant contents and disclosure of which are hereby incorporated by reference.

According to embodiments of the present invention, a polynucleotide encoding a protein or peptide having a sequence that is at least 90% or at least 95% homologous to human ILK protein (FIG. 1; SEQ ID NO: 1) or a functional fragment thereof, with or without the corresponding R211A mutation or substitution, may be administered to a cell in vitro or in vivo either transiently or stably using non-viral vectors or as naked DNA or RNA according to any known method or technique, such as by transfection, electroporation, gene gun, micro-injection, etc. According to some embodiments, a polynucleotide of the present invention may be administered to a cell in vitro or in vivo using any endocytic approach and/or delivery reagent known in the art to deliver a polynucleotide into the interior of a cell, such as by using emulsions, micelles, nanoparticles, liposomes, which may be charged, non-charged and/or conjugated, LIPOFECTIN®, LIPOFECTAMINE®, CELLFECTIN®, microcapsules, artificial virus envelopes, and the like to enclose or package the polynucleotide for delivery into the cell. The delivery reagent may be modified via any known means to improve its targeted delivery to particular cells or tissue(s)—e.g., cardiac cells, such as through the use of antibodies or ligands, or to reduce its unwanted degradation, clearance or recognition by the immune system if administered in vivo, such as by using opsonization-inhibiting moieties including PEG and the like or other molecules or moieties known in the art for this purpose. See, e.g., U.S. Pat. Nos. 7,811,992; 7,790,140; 7,128,912; 7,517,864; and 4,837,028, the relevant contents and disclosure of which are hereby incorporated by reference. Alternatively, available cardiac targeting methods may be used, such as antibody-mediated and ultrasound-mediated bubble destruction. See, e.g., Hernot, S. et al., "Effect of High-Intensity Ultrasound-Targeted Microbubble Destruction on Perfusion and Function of the Rat Heart Assessed by Pinhole-Gated Spect," *Ultrasound in Med. & Biol.* 36(1):158-165 (2010), the entire contents and disclosure of which is hereby incorporated by reference.

According to some method embodiments of the present invention, a composition comprising a mammalian integrin-linked kinase (ILK) protein or peptide having a sequence that is at least 90% or at least 95% homologous to human ILK protein (FIG. 1; SEQ ID NO: 1) or a functional fragment thereof may be administered to a mammalian or human cell in vitro or in vivo, such as a cardiac stem cell, mesodermal cell, mesenchymal cell, primary cultured cardiac cell, cardioblast, cardiomyocyte, or any other cardiac cell including a heart precursor or progenitor cell, a heart smooth muscle or endothelial cell, or to an induced pluripotent stem (iPS) cell. Such a cell may generally be any cell or cell type capable of differentiation into a cardiac cell or cardiac cell type, which may be normally found in the heart of a mammal, such as a human.

According to some embodiments, a composition administered to such a cell in vitro or in vivo may be a composition comprising a mutant mammalian integrin-linked kinase (ILK) protein or peptide, such as a composition comprising a protein or peptide having a sequence that is at least 90% or at least 95% homologous to human ILK protein (FIG. 1; SEQ ID NO: 1) or a functional fragment thereof, wherein the ILK protein or peptide has a mutation or substitution at a position corresponding to amino acid residue 211 of wild-type human ILK (numbered from the N-terminus of the full length protein sequence as shown in FIG. 1) that replaces the arginine (R) at such position with another amino acid, such as alanine (A). For example, the composition may comprise human ILK_R211A protein (SEQ ID NO: 2), or a functional fragment thereof.

According to method embodiments of the present invention, a composition comprising a protein or peptide having a sequence that is at least 90% or at least 95% homologous to human ILK protein (FIG. 1; SEQ ID NO: 1) or a functional fragment thereof, with or without the corresponding R211A mutation or substitution, may be administered to a cell according to any technique or approach known or available in the art for administering a protein or peptide into the interior of a cell either in vitro or in vivo. According to some embodiments, an ILK protein or peptide of the present invention may be administered to a cell in vitro or in vivo using any endocytic approach and/or delivery reagent known in the art to deliver a peptide or protein into the interior of a cell, such as by using emulsions, micelles, nanoparticles, liposomes, which may be charged, non-charged and/or conjugated, LIPOFECTIN®, LIPOFECTAMINE®, CELLFECTIN®, microcapsules, artificial virus envelopes, and the like to enclose or package the peptide or protein for delivery into the cell. The delivery reagent may be modified via any known means to improve its targeted delivery to particular cells or tissue(s)—e.g., cardiac cells, such as through the use of antibodies or ligands, or to reduce its unwanted degradation, clearance or recognition by the immune system if administered in vivo, such as by using opsonization-inhibiting moieties including PEG and the like or other molecules or moieties known in the art for this purpose. ILK-based proteins or peptides administered according to some embodiments of the present invention may further include a protein transduction domain (PTD) attached to the protein or peptide. See, e.g., Zhou H et al., "Generation of induced pluripotent stem cells using recombinant proteins," *Cell Stem Cell* 4(5):381-384 (2009); and Takenobu T et al., "Development of p53 protein transduction therapy using membrane-permeable peptides and the application to oral cancer cells," *Mol Cancer Ther* 1(12):1043-1049 (2002), the relevant contents and disclosure of which are hereby incorporated by reference.

According to some method embodiments, a composition administered to a cell either in vitro or in vivo may comprise shorter peptides, fragments and/or peptide mimetics based on the sequence of ILK or ILK_R211A. Such peptides, fragments and/or peptide mimetics may be used according to any known technique to increase their bioavailability, and their administration may generate even smaller peptide fragments through proteolysis, such as by serum proteases or other proteases, which may augment the efficacy of the parent molecule.

According to embodiments of the present invention, a composition comprising an ILK-based protein, peptide, peptide mimetic or fragment or comprising a polynucleotide encoding the same as described above may be administered either to cells in vitro or to heart or cardiac tissue of an individual to be treated directly in vivo. When such a composition is applied directly to heart or cardiac tissue in vivo, any known surgical technique may be used to access the heart. According to these embodiments, the composition may be applied or administered by injection into heart or cardiac muscle or tissue, by placing the composition on or adjacent to heart or cardiac muscle or tissue, and/or by intracoronary artery or systemic infusion or injection, which may be performed at the time of percutaneous coronary angioplasty and/or stenting procedures.

According to embodiments of the present invention, cellular-based approaches may be used to treat an individual. According to these embodiments, once a composition comprising an ILK-based protein, peptide, peptide mimetic or fragment or comprising a polynucleotide encoding the same as described above is administered to a cell(s) in vitro, ex vivo or in culture, such a cell(s) may then be administered, transferred or transplanted to heart or cardiac tissue of an individual to be treated. According to these embodiments, the cell(s) may be administered, transferred or transplanted to heart or cardiac tissue of an individual to be treated according to any known surgical technique that may be used to access the heart of the individual. The cell(s) may be applied or administered by injection into heart or cardiac muscle or tissue, by placing the cell(s) on or adjacent to heart or cardiac muscle or tissue, and/or by intracoronary artery or systemic infusion or injection, which may be performed at the time of percutaneous coronary angioplasty and/or stenting procedures. Such cell(s), which have been administered a composition comprising an ILK-based protein, peptide, peptide mimetic or fragment or composition comprising a polynucleotide encoding the same as described above, may include a mammalian or human cell in vitro or ex vivo, such as a cardiac stem cell, mesodermal cell, mesenchymal cell, primary cultured cardiac cell, cardioblast, cardiomyocyte, or any other cardiac cell including a heart precursor or progenitor cell, a heart smooth muscle or endothelial cell, or an induced pluripotent stem (iPS) cell.

According to some embodiments, the cell(s) that have been administered such a composition may have been cultured as primary cells from an individual ex vivo, such as from the heart of an individual, and such treated or administered cell(s) may then be administered, transferred or transplanted back into the same individual, such as the heart of the same individual, such as by autographic transplantation. Alternatively, the cell(s) that have been administered such a composition may have been cultured as primary cells from an individual ex vivo, such as from the heart of an individual, and such treated or administered cell(s) may then be administered, transferred or transplanted into a different individual, such as the heart of a different individual, such as by allographic, isographic or xenographic transplantation. According to some embodiments, the cell(s) that have been administered such a composition may be used in combination with other cells, tissue and/or graft used for the transplantation, which may be used to improve engraftment, survival and/or differentiation capacity of cellular transplants. Cells may be taken from an individual according to any surgical or other method known in the art for extracting, biopsying, etc., cells from an individual by surgery, syringe, etc.

According to embodiments of the present invention, a composition comprising an ILK-based protein, peptide, peptide mimetic or fragment or comprising a polynucleotide encoding the same as described above, or a composition comprising cell(s) administered or treated in vitro, ex vivo or in culture with a composition comprising an ILK-based protein, peptide, peptide mimetic or fragment or comprising a polynucleotide encoding the same as described above, may be administered to an individual, such as a human individual, having or at risk of developing heart failure or impaired cardiac function. Such an individual having or at risk of developing heart failure may include an individual having, having had or at risk of developing an acute myocardial infarction, an ischemic condition, disease or syndrome, a cardiomyopathy (familial, idiopathic, primary or secondary to cardiotoxic drugs such as doxorubicin), such as adult or childhood forms of dilated cardiomyopathy (DCM), hypertensive cardiomyopathy, etc., a congenital heart defect, valvular heart disease, and/or postsurgical cardiac dysfunction for congenital or acquired heart disease. Such a composition may also be used to promote healing, remodeling and/or beneficial hypertrophy of heart tissue following either acute or chronic heart damage or ischemic conditions in an individual, such as a human individual.

It is envisioned that the discovery of an ILK mutant protein that displays the ability to trigger beneficial signaling in a cell autonomous manner while avoiding or resisting potentially oncogenic effects of exogenous growth factor and/or PI3K activation lead to the identification of a platform for the development of engineered kinase mutations having selected activities and/or peptides that interfere with selected protein-protein and protein-lipid interactions for treatments against a variety of diseases (cardiac, neural, cancer), including anti-oncogenesis and neuroprotection. Furthermore, the discovery that Hsp70/Hsc70 interacts with and binds to the mutant ILK_R211A protein and increases its expression and signaling presents a new paradigm for the development of new therapies.

According to some putative embodiments, a composition comprising an ILK-based protein or peptide or polynucleotide encoding the same, or a cellular-based approach utilizing an ILK-based protein or peptide or polynucleotide encoding the same, in neuronal cells or their precursors is envisioned for use as a treatment for ischemic neurological disorders such as stroke, in which cases the effects of the ILK-based protein or peptide may be predicted to be cytoprotective for similar reasons. Likewise, such a composition may also be expected to be beneficial for use as a treatment for neurodegenerative diseases, such as Alzheimer's disease (AD), Huntington's disease (HD), and multiple sclerosis (MS), since ILK deactivates GSK-3l3, a critical target in misfolded protein disorders, and activates cytoprotective, anti-apoptotic signaling. Moreover, such a composition may also be expected to be beneficial for use as a treatment for pulmonary arterial or venous hypertension of diverse causation, since the PI3K pathway is hyperactivated in these disorders.

According to other putative embodiments, it is envisioned that detection of ILK protein, such as in the bloodstream, may be used as a biomarker for cardiac disease, since it is highly expressed in diseased hearts and may be released upon cardiac tissue damage.

According to other putative embodiments, it is envisioned that a peptide screen may be used to discover novel efficacious peptides, perhaps modeled on the mutant ILK_R211A protein, in order to identify and optimize cardioprotective and/or anti-oncogenic properties, and to facilitate therapeutic formulation. Such peptides may be modeled or rationalized based on the known structural domains of ILK. ILK is a multi-domain kinase comprised of an ankyrin repeat domain (ANK), a PH domain, and a catalytic kinase domain (KD). The ILK ANK repeat mediates binding to the adaptor protein PINCH (particularly interesting new Cys-His protein). See, e.g., Velyvis A et al., "Solution structure of the focal adhesion adaptor PINCH LIM1 domain and characterization of its interaction with the integrin-linked kinase ankyrin repeat domain," $J$ $Biol$ $Chem$ 276(7):4932-4939 (2001). The PH domain is critical for PIP3-mediated membrane binding and activation of the ILK KD, thereby acting as a signal-regulated membrane targeting module. Thus, peptides may be rationalized according to the intended therapeutic application. For example, based in part on the observations of the ILK_R211A mutant protein, the disruption of interactions between the ILK PH domain and other proteins or factors is predicted to interfere with ILK activation (through competition to PIP3 binding) and exhibit anti-oncogenic effects in cancer cell lines harboring PI3K mutations. Short peptides having a sequence corresponding or homologous (e.g., greater than 90% or 95% homologous) to the PH domain of ILK (defined as amino acids 180 through 212 of the human ILK protein sequence shown in SEQ ID NO: 1) and ranging in size from a few amino acids to the entire length of the PH domain or greater may be used to competitively inhibit interactions between the PH domain of the endogenous ILK in a cell and other proteins or factors. Therefore, putative embodiments may include compositions comprising such peptides and/or polynucleotides encoding such peptides as well as methods of using them. Conversely, truncated or deletion proteins or peptides comprising the ILK KD alone or linked to a mutant PH or ANK domain, would be predicted to exhibit cytoprotective properties that are delinked from potential oncogenic signaling. ILK domain deletion mutants may also be synthesized according to known methods and developed as drugs per se, or used as framework peptide structures for creating additional randomized point mutations, as directed by functional assays.

According to these peptide screening embodiments, the ILK-based peptides may be screened for phenotypic effects based on disease-specific assays or cytoprotective and/or anti-oncogenic effects, and the screen may be performed using either the ILK-based peptide directly or expression of the ILK-based peptide from a polypeptide introduced to cells of a testing platform including, for example, iPS-derived human cardiomyocytes, or human cardiac fibroblasts derived from patient samples of idiopathic childhood DCM. iPS-derrived cardiomyocytes obtained from Cellular Dynamics have been shown to form homogeneous contractile syncitia phenotype for up to 2 weeks in vitro, and exhibit typical electrophysiological responses to pharmacological agents. These test cells may also be subjected to doxirubicin (DOXO) to compare dose-response curves based on cardiomyocyte viability with or without the tested peptide. Induction of a cardiomyogenic signal (e.g., nkx2.5, GATA4, Islet-1 expression) or expression of Hsp70 and/or SERCA2 (measured as a SERCA2/PLB ratio) in the test cells may also be used as a test criteria, and vincristine may be used as an anti-apoptotic control. According to some screening embodiments, standard assays (proliferation, apoptosis, clonogenic growth in soft agar) may be used to survey anti-oncogenic properties of ILK peptides using cancer cell lines, such as breast, lung, prostate, liver, and colon cancer cell lines, which may be arrayed in a 96-well format.

According to other putative embodiments, a composition comprising an ILK-based protein or peptide or polynucleotide encoding the same, or a cellular-based approach utilizing an ILK-based protein or peptide or polynucleotide encoding the same, is envisioned for use as a treatment for cancer. For example, ILK_R211A may be predicted to inhibit oncogenic signaling resulting from mutations in PTEN and/or PI3K pathways found in many cancers, based on its dominant negative effects, such as through competition for interaction with target molecules in these pathways.

According to other putative embodiments, ILK-based proteins and peptides may be developed based on the paradigm of invoking Hsp70-enhanced function of engineered mutations in cytoprotective kinases, such as PKB/Akt and PKCE, to achieve enhanced efficacy/toxicity profiles. Engineered mutations in signaling kinases, such as ILK, PKB/Akt or PKC, may be exploited to alter their mode of action, efficacy and/or toxicity profiles, such as through induction of a heat-shock protein response.

Having described the many embodiments of the present invention in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

EXAMPLES

Example 1

ILK Promotes Cardiomyogenesis in the Human Heart

It is presently hypothesized that the cardioprotective effects of ILK may in part derive from its capacity to induce cardiomyogenesis from susceptible precardiomyocytic progenitor cells. Accordingly, it is demonstrated herein that experimental over-expression of ILK in primary cultures of cells derived from human fetal hearts induces high frequency differentiation of tissue-resident cardiac progenitor cells into cardioblasts and accelerated maturation of immature cardioblasts into cardiomyocytes. Overexpression of ILK is also shown to induce cardiomyogenesis in cultures of cardiac cells enzymatically isolated from samples obtained during surgical correction of hearts of patients with tetralogy of Fallot (TF) and explanted hearts with DCM. It is presently proposed that ILK overexpression may effectively bypass the requirement for transduction of growth factor-mediated differentiation signals. Since ILK may be activated by hypoxia, which normally occurs during fetal heart development (see, e.g., Fudim M B J et al., "The influence of hypoxia on generation, expansion and differentiation of unrestricted somatic stem cells from human cord blood and bone marrow stromal cells," *Proc of ISSCR Conf* 2009, Page 175, the contents and disclosure of which are hereby incorporated by reference) and in postnatal heart disease, the present findings supports the paradigm that stress induction of ILK might serve as a novel regulator of cardiomyogenesis.

Example 1

Methods

Isolation and Cell Culture. Human fetal hearts were harvested during elective pregnancy termination at 19 to 22 weeks gestation, in accordance with the guidelines of the Institutional Human Research Ethics Board of the Hospital for sick Children and after obtaining maternal consent. The hearts were minced and washed with phosphate-buffered saline. Cells isolation was performed with 0.2% trypsin and 1 mg/ml type II collagenase in 0.02% glucose phosphate-buffered saline (PBS), pH 7.4 solution at 37° C. After dissection, cells were incubated on plastic culture dishes (Sarstedt, Inc, Newton, N.C.) for 2 hours at 37° C. to separate cells for adherent and non-adherent cells, with Iscove modified Dulbecco medium (IMDM, Gibco, Invitrogene Corporation, Carlsbad, Calif.) containing penicillin and streptomycin and supplemented with 10% fetal bovine serum (FBS, Gibco). After incubation the supernatant with non-adherent cells was transferred to new culture dishes (Sarstedt). Both adherent and non-adherent cells were placed in a 5% carbon dioxide incubator at 37° C. prior to infection.

In vitro Studies using ILK Adenoviral Infection. Cells were cultured to 60%-70% confluency prior to adenovirally mediated infection with ILK constructs containing green fluorescent protein (GFP), in replication-deficient serotype 5 adenovirus encoding either the human wild-type ILK gene incorporating GFP construct (Ad-ILK$^{WT}$) or ILK_R211A previously shown to modulate ILK expression and activity in human fetal cardiomyocytes or an empty GFP virus construct (control). See, e.g., Traister et al., (2009), supra. Cells were infected at 37° C. at multiplicity of infection of 1.5 in IMDM with 10% FBS for 24 hours and analyzed 3-5 days after infection with or without passage. The infection efficiency was confirmed by more than 80% GFP positivity.

Western Blots. For western blot analysis, total and phopsho-specifc protein expression was measured in lysates derived from human fetal cardiomyocytes in culture and from transgenic and control mouse ventricular tissue as described previously. See, e.g., Lu H et al., (2006), supra. Briefly, cells extracts were prepared by lysing the cells for 20 min on ice in RIPA lysis buffer (150 mM NaCl, 1% Nonidet P40, 05% deoxycholate, 0.1% SDS, 50 mM Tris, pH 8.0, and 1 mM PMSF). The expression levels of the proteins was assessed using the following primary antibodies: rabbit monoclonal anti-ILK (Clone 4G9, Cell Signaling Technologies), rabbit polyclonal anti-Isl1 (Chemicon International, Inc), mouse monoclonal anti-β-catenin (Clone E-5, Santa Cruz Biotechnology, Inc), mouse monoclonal anti-active-β-catenin (Clone 8E7, Millipore), monoclonal anti-GAPDH (Clone GAPDH-71.1, Sigma), mouse monoclonal anti-myosin heavy chain-13 (Clone A4.951, Santa Cruz Biotechnology, Inc), rabbit polyclonal anti-α myosin heavy chain (Sigma). After incubation with the primary antibody, the blots were washed and incubated for 1 h with the appropriate horseradish peroxidase-conjugated secondary antibody (Jackson ImmunoResearch Laboratories). Proteins were visualized with an enhanced chemiluminescence (ECL) detection reagent (Amersham Pharmacia Biotech) and quantified by densitometry.

Immunohistochemical Analysis. Cultured cells on coverslips were maintained in culture for 4-7 days and then fixed with 4% paraformaldehyde for 10 min at room temperature. Following rinsing with PBS, cells were permeabilized with 0.1% Triton-X 100 (Sigma) for 15 min and then blocked with normal goat serum or 5% milk for 30 min and subjected to immunostaining. The following primary antibodies were used in this study: rabbit polyclonal anti-vimentin (Abcam Inc), rabbit monoclonal anti-ILK (Clone 4G9, Cell Signaling Technologies), mouse monoclonal anti myosin heavy chain-β (Clone MF-20, provided by Dr. Donald A. Fischman, Cornell University Medical College, NY), mouse monoclonal anti-nkx2.5 (Clone 259416, R&D Systems), mouse monoclonal anti α-actin (Clone 1A4, Santa Cruz Biotechnology, Inc), rabbit polyclonal anti-ki-67 (Millipore). Nuclei were stained with 4,6-diamino-2-phenylindole (DAPI). All analysis was done with OpenLab 4.0.2 software (Agilent Technologies, Scientific Software Inc, Palo Alto, Calif.).

Semi-quantitative Reverse Transcription-PCR (RT-PCR). Total RNA from cultured cells or heart tissue was prepared by using TRIzol® (Invitrogen) according to the manufacturer's instructions. Total RNA (1 µg) was reverse-transcribed with the SuperScript First-strand Synthesis System (Invitrogen). The cDNA of targeted genes was then amplified using the following primers: mouse Isl1: 5'-CGTGCAGACCACGAT-GTGG-3' (SEQ ID NO: 3) and 5'-GACTGAGGCCCGT-CATCTC-3' (SEQ ID NO: 4); human Isl1: 5'-CACGATCAG-TATATTCTGAG-3' (SEQ ID NO: 5) and 5'-CGTGGTCTGCTCGGCAGAAG-3' (SEQ ID NO: 6). A total of 30 amplification cycles were performed. To control for the amount of intact RNA, GAPDH was amplified in parallel with the following primers: mouse GAPDH: 5'-AGGGCTGCCATTTGCAGTGG-3' (SEQ ID NO: 7) and 5 CATTTGATGTTAGTGGGGTCT-3' (SEQ ID NO: 8); and human GAPDH: 5'-CGGATTTGGTCGTATTGGGC-3' (SEQ ID NO: 9) and 5'-CTCCATGGTGGTGAAGACG-3' (SEQ ID NO: 10).

Transmission Electron Microscopy (EM). For electron microscopic analysis, cells were fixed for 10 min in 1% glutaraldehyde 4% formaldehyde mixture in PBS, scraped off and pelleted. Fixation was continued for 1 h. After fixation, the cells were post-fixed in 1% solution of osmium tetroxide and dehydrated in graded acetone at 4° C. After embedding and polymerization, 0.5-µm-thick sections were initially cut with a Leica Ultracut UCT ultramicrotome, stained in uranyl acetate and lead citrate, and observed with transmission electron microscopy at 80 kV using a Philips CM100 transmission electron microscope.

Mice. The methods for generation of transgenic animals conveying cardiac-specific overexpression of wild type human ILK gene (ad-ILK$^{WT}$) have been previously described. See, e.g., Lu H et al., (2006), supra. Mice are genotyped by polymerase chain reaction (PCR) as described in the original reports.

Statistics. Statistical comparison of ILK-specific effects relied on a paired t test or analysis of variance (ANOVA) followed by linear contrast tests to assess differences among groups using SAS12.0 (Cary, N.C.). The significance level was set at $P<0.05$.

The acquisition of human heart samples was approved by an institutional review ethics committee and all subjects gave informed consent to the study. The mouse studies were approved by The Animal Care Committee at the Hospital for Sick Children.

Example 1

Summary

Primary cultures of human fetal myocardial cells (19-22 weeks gestation) are shown to yield scattered aggregates of cardioblasts (positive for nkx2.5 and containing nascent sarcomeres). Adenovirus-mediated overexpression of ILK (~2-fold) robustly increases the number of new aggregates of primitive cardioblasts ($p<0.001$), as well as the number of more differentiated individual cardiomyocytes ($p<0.001$). This effect of ILK is accompanied by activation of β-catenin and increase in expression levels of Islet-1 ($p<0.001$), which is also observed in transgenic mice with cardiacspecific overexpression of ILK ($p<0.001$). Interestingly, these effects of ILK are greater with higher ILK expression levels (~3-fold) using a mutant ILK deficient in agonist-induced phosphoinositide 3-kinase (PI3K) signaling (ILK_R211A) ($p<0.001$). It is therefore proposed that in the human fetal heart, ILK activation may instruct the differentiation of mesodermal progenitor cells into a cardioblasts, as well as their further maturation towards differentiated cardiomyocytes, while bypassing proximal PI3K activation normally required for transduction of growth factor-mediated differentiation signals. It is also reported that adenoviral over-expression of ILK coincides with de novo appearance of nkx2.5 expressing cells in cardiac cell cultures derived from samples of human dilated cardiomyopathy (DCM) and tetralogy of Fallot (TF). Altogether, the present data indicates that ILK plays an important role in promoting human cardiomyogenesis in diverse conditions and diseases.

Example 1

Results

Figure 2B:
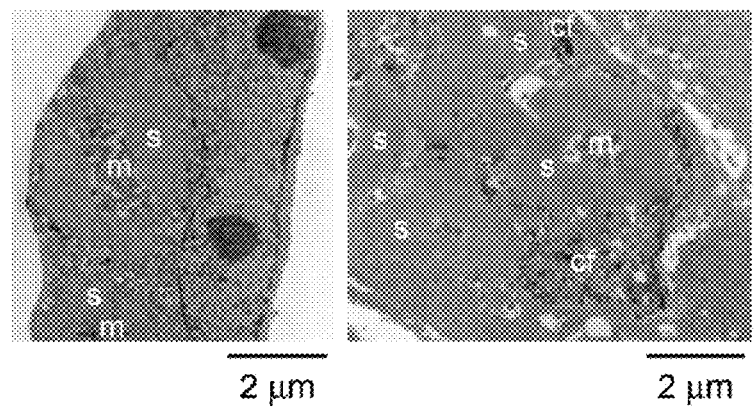
FIG. 2B is a pair of transmission electron microscopy images of cultures of cells freshly isolated from human fetal myocardium at day 2 containing primitive cardioblasts with nascent sarcomeres (s) and mitochondrial (m) clusters (left) and cells with the transitional features containing both nascent sarcomeres and deep invaginations containing collagen fibers (cf) (right).
Figure 2C:
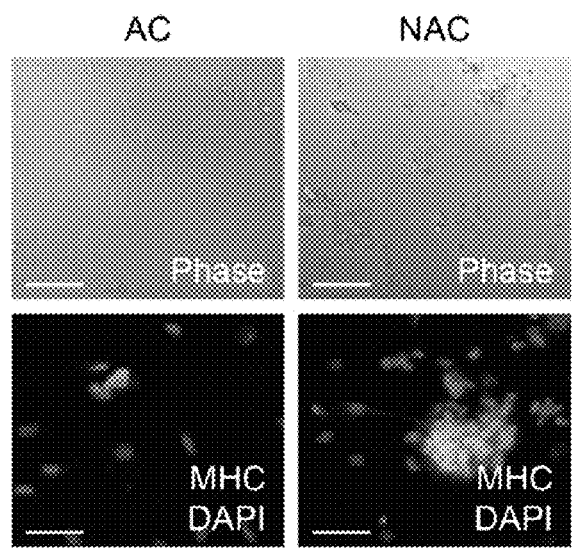
FIG. 2C is a set of phase contrast images (upper panel) and fluorescence images (lower panel) showing adherent (AC) and non-adherent (NAC) cells at 2 days after isolation. Immunostaining with anti-β-MHC antibody demonstrates that non-adherent clusters consist mainly of β-MHC positive cardioblasts. Scale bar 80 μm (for phase) and 25 μm (for fluorescence imaging).

Adenoviral-mediated over-expression of ILK in cultures of cells isolated from human fetal myocardium is shown to enhance the formation of aggregates of cardioblasts. FIG. 2 provides a description of the primary cultures of cells derived from fetal myocardium. Initial immuno-histochemical screening demonstrated that the majority of cells isolated from human fetal myocardium (19-22 weeks gestation) were positive for the fibroblast-specific marker, vimentin. See also, e.g., Ieda M et al., "Cardiac fibroblasts regulate myocardial proliferation through beta1 integrin signaling," *Dev Cell*, 16(2):233-244 (2009), the entire contents and disclosure of which are hereby incorporated by reference. Approximately 35% cells were also positive for the early cardiac lineage marker nkx2.5, and approximately 20% of cells were positive for cardiomyocyte-specific sarcomeric proteins such as α-actinin, as well as β-myosin heavy chain (β-MHC) and α-actin which are typically expressed in fetal ventricular cardiomyocytes (FIGS. 2A and 2C). See, e.g., Engel F B et al., "A mammalian myocardial cell-free system to study cell cycle reentry in terminally differentiated cardiomyocytes," *Circ Res*, 85(3):294-301 (1999), the entire contents and disclosure of which are hereby incorporated by reference. Rare cells (<about 5%) demonstrated the presence of smooth muscle cell α-actin (data not shown). Electron microscopy confirmed that cardioblasts contained nascent sarcomeric structures (FIG. 2B). Many of these cells exhibited with a tight connection with extracellular collagen fibers (in some cases filling their invaginations) that were likely produced before their cardiogenic commitment (FIG. 2B).

Primary cultures of myocardial cells were pre-incubated for 2 hours to separate the non-adherent fraction enriched for cardiomyocytes from the adherent fraction containing the remaining mixed population of myocardial cells (FIG. 2C). In the human fetal heart digests, it is shown by immunostaining and by EM that non-adherent cells were mainly comprised of uniform aggregates of immature cardioblasts containing nascent sarcomeres adjacent to abundant clusters of mitochondria. This fraction of initially floating and aggregating cells attached to the bottom of the culture dishes after 24 hours of incubation. In contrast, the initially adherent cells were uniformly spread and did not aggregate (FIG. 2C). This phenotypically diversified fraction of adherent cells contained fibroblasts, smooth muscle cells, endothelial cells and a subset of non-differentiated mesodermal cells.

Figure 3A:
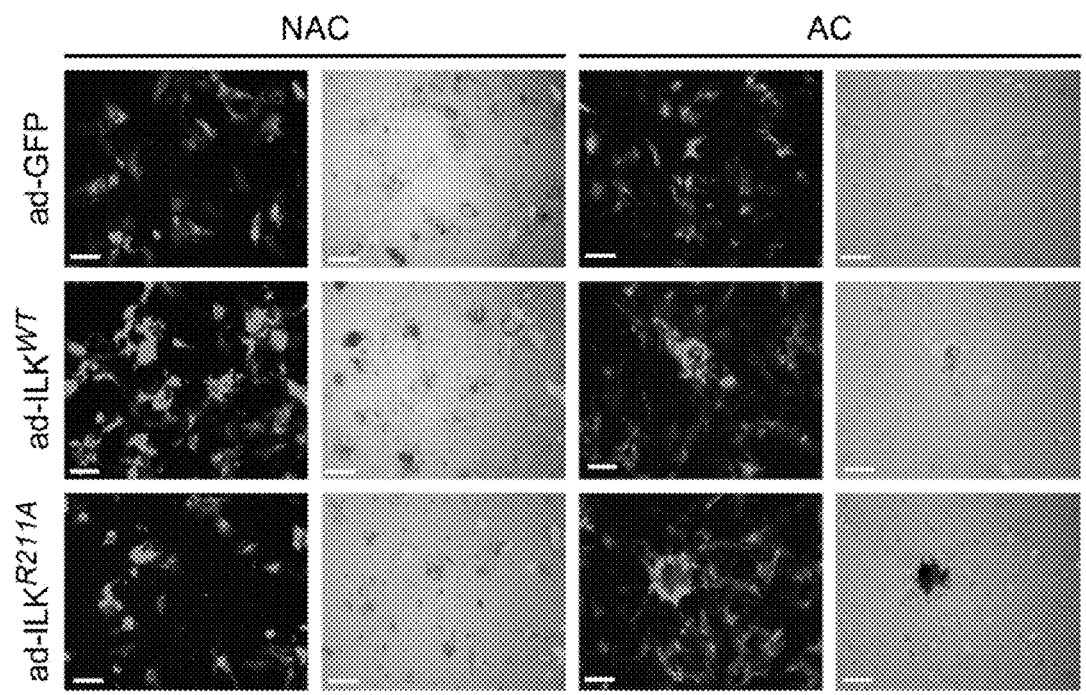
FIG. 3A is a set of fluorescence microscopy images of adherent (AC) and non-adherent (NAC) cells and their composites with the phase contrast images identifying the cells transduced with GFP-linked vectors (ad-GFP), wild type ILK vector (ad-ILK$^{WT}$) and mutant ILK vector (ad-ILK_R211A). Scale bar 80 μm.
Figure 3B:
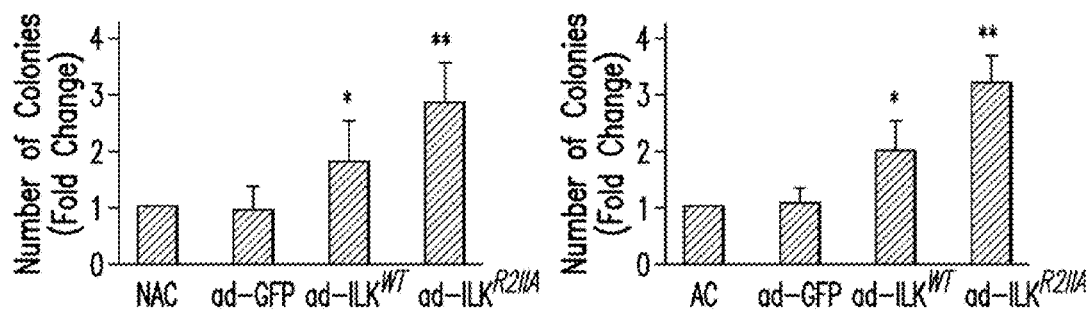
FIG. 3B is a bar graph showing quantification of cell aggregates in AC (right panel) and NAC (left panel) infected with ad-ILK$^{WT}$, ad-ILK_R211A and ad-GFP versus non-infected cells. Bar graphs represent mean values±SD, n=10 (random fields), *p<0.02, **p<0.02 (for AC) and *p<0.001, **p<0.0001 (for NAC).
Figure 3C:
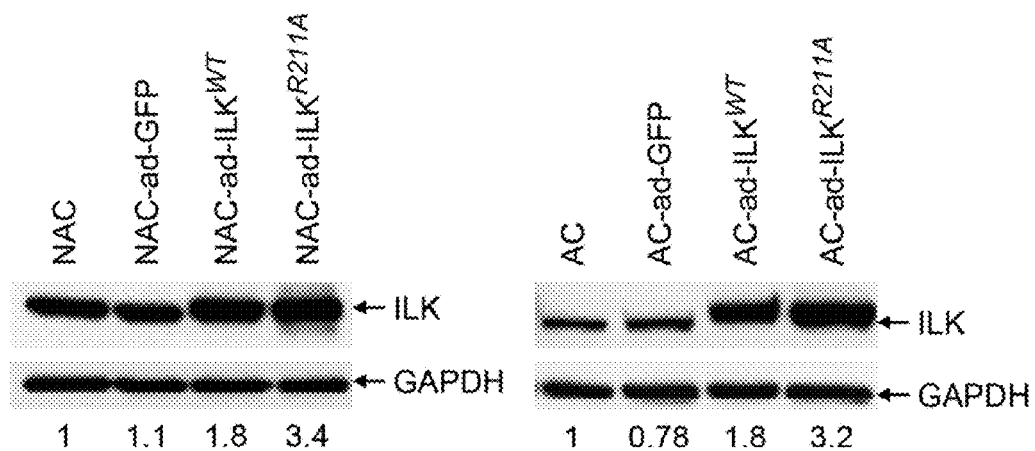
FIG. 3C is a set of images of Western blots demonstrating a progressive increase in the level of ILK expression in AC and NAC transduced with ad-ILK$^{WT}$ or ad-ILK_R211A as compared to non-transduced cells and cells transduced with the vector bearing the GFP-encoding message only. GAPDH was used as a loading control. Numerical values below each lane in this representative blots indicate ILK protein levels normalized to GAPDH.

To determine the effects of ILK over-expression on cardiogenic morphogenesis, both adherent and non-adherent cells were adenovirally transduced with cDNA encoding human wild type ILK-GFP construct (ad-ILK$^{WT}$) or empty adenoviral GFP control (ad-GFP). FIG. 2 shows that over-expression of ILK induces cellular aggregation in cultures of adherent cells and increases the number of aggregates in cultures of initially non-adherent cells. It was found 4 days after transduction that approximately 80% of cells expressed GFP in both adherent and initially non-adherent fractions of myocardium-derived cells indicating high efficiency of transduction (FIG. 3A). The ad-ILK$^{WT}$-transduced cultures yielded numerous spherical aggregates, representing about 2-fold increase compared to non-transduced control cultures and to cultures transduced with the empty vector alone ($p<0.001$) (FIG. 3B). Moreover, ad-ILK$^{WT}$ induced aggregates were comprised of GFP positive cells, whereas the sparse aggregates in the control groups did not show conspicuous GFP staining. The increased levels of ILK protein expression in ad-ILK$^{WT}$ cultures was confirmed by Western blot analysis (FIG. 3C). To test the requirement for PI3K activation in the ILK-mediated cardiomyogenic effect, over-expression of a mutant ILK gene deficient in PIP3 binding as a result of a point mutation in its PH domain (ILK_R211A) was used. See, e.g., Lu H et al., (2006), supra. Surprisingly, our results indicate that ILK_R211A-treated cultures demonstrate higher levels of ILK protein expression (approximately 3-fold increase) as compared to ad-ILK$^{WT}$ infected cultures (FIG. 3C). Ad-ILK_R211A treatment also resulted in significant increase in the number of cellular aggregates, detected in both the initially adherent as well as non-adherent cardiac cell populations ($p<0.001$ vs ad-ILK$^{WT}$ and GFP controls) (FIG. 3B). These results suggest that ILK over-expression acts in a cell-autonomous manner to effectively bypass the requirement for exogenous growth factor-mediated PI3K activation in the induction of cardiomyogenesis.

Figure 4A:
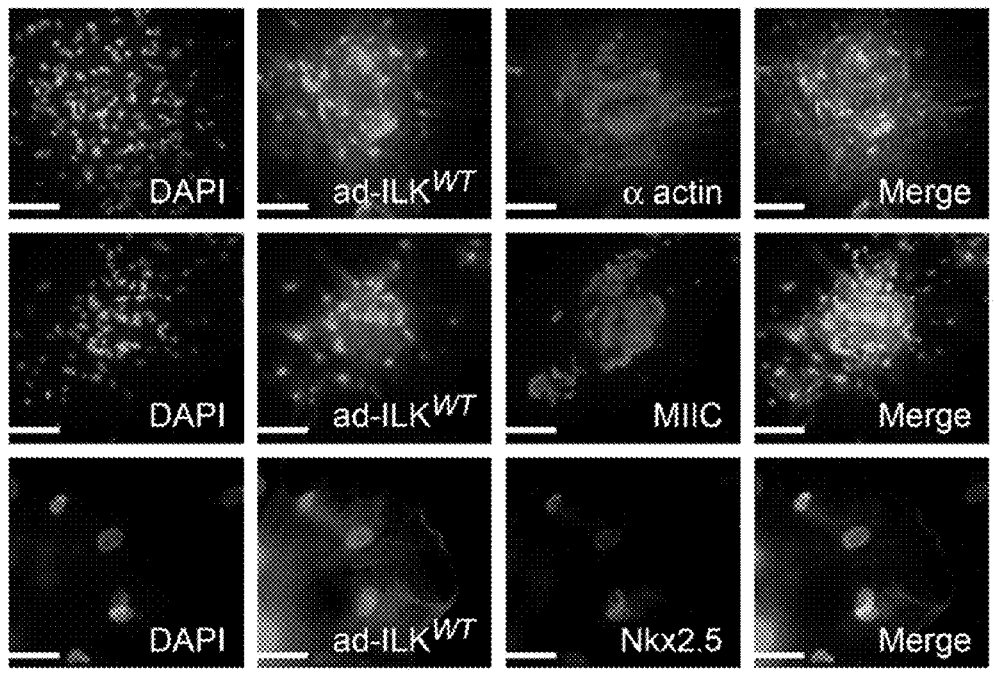
FIG. 4A shows immune-cytochemistry images indicating that cellular aggregates present in the ILK$^{WT}$-transduced cultures contain numerous cardioblasts displaying the presence of α-actin, β-MHC and nkx2.5 (all marked with red rhodamine). Nuclei were identified with blue DAPI, and expression of ILK was marked with green GFP. In top and middle panels, scale bars represent 80 μm; in the bottom panel, scale bar represents 25 μm.
Figure 4B:
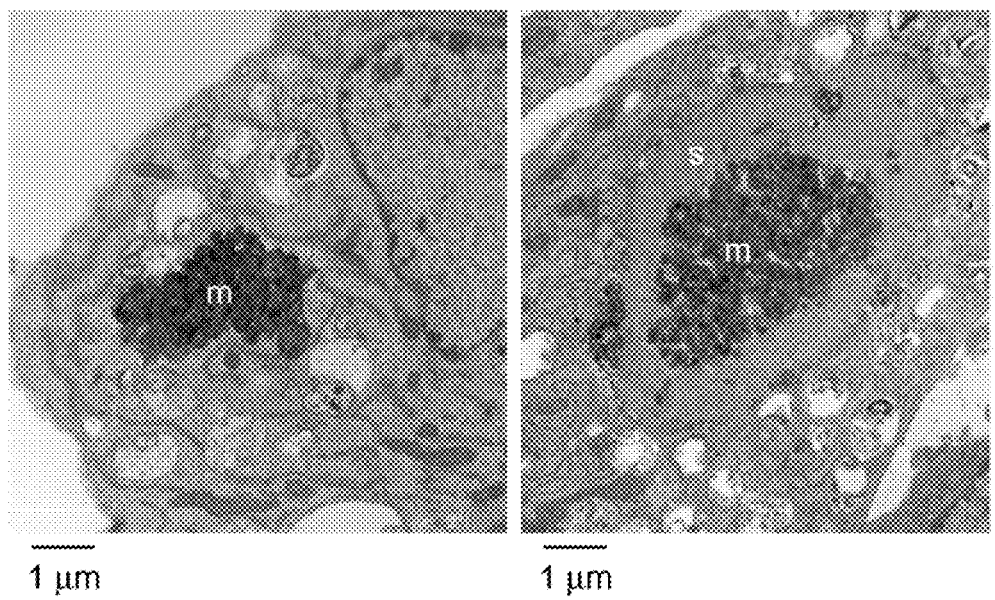
FIG. 4B is a pair of transmission electron microscopy images showing clusters of mitochondria (m) in the cytoplasm of the primitive cardioblast (left), whereas the more differentiated cells (right panel) contained similar mitochondrial clusters (m) located in close proximity to nascent sarcomeres (s).

To further characterize the content of cell aggregates in response to ILK upregulation, cultures of transduced cells were probed with antibodies to the early cardiac lineage marker nkx2.5, the cardiomyocyte markers α-actinin and β-MHC, and to α-SMA, a smooth muscle actin-specific marker to characterize ILK-induced cardioblasts. FIG. 3 shows that aggregates in ILK-overexpressing cultures are mostly composed of cardiomyoblasts. Aggregates induced by ad-ILK$^{WT}$ or ad-ILK_R211A, and even those sparse aggregates in ad-GFP and noninfected control cells, prevalently consisted of cells having cardioblast marker nkx2.5 and the sarcomeric protein marker β-MHC (FIG. 4A). EM of constituent cells revealed corresponding sarcomeric structures of variable maturation (FIG. 4B).

Figure 5:
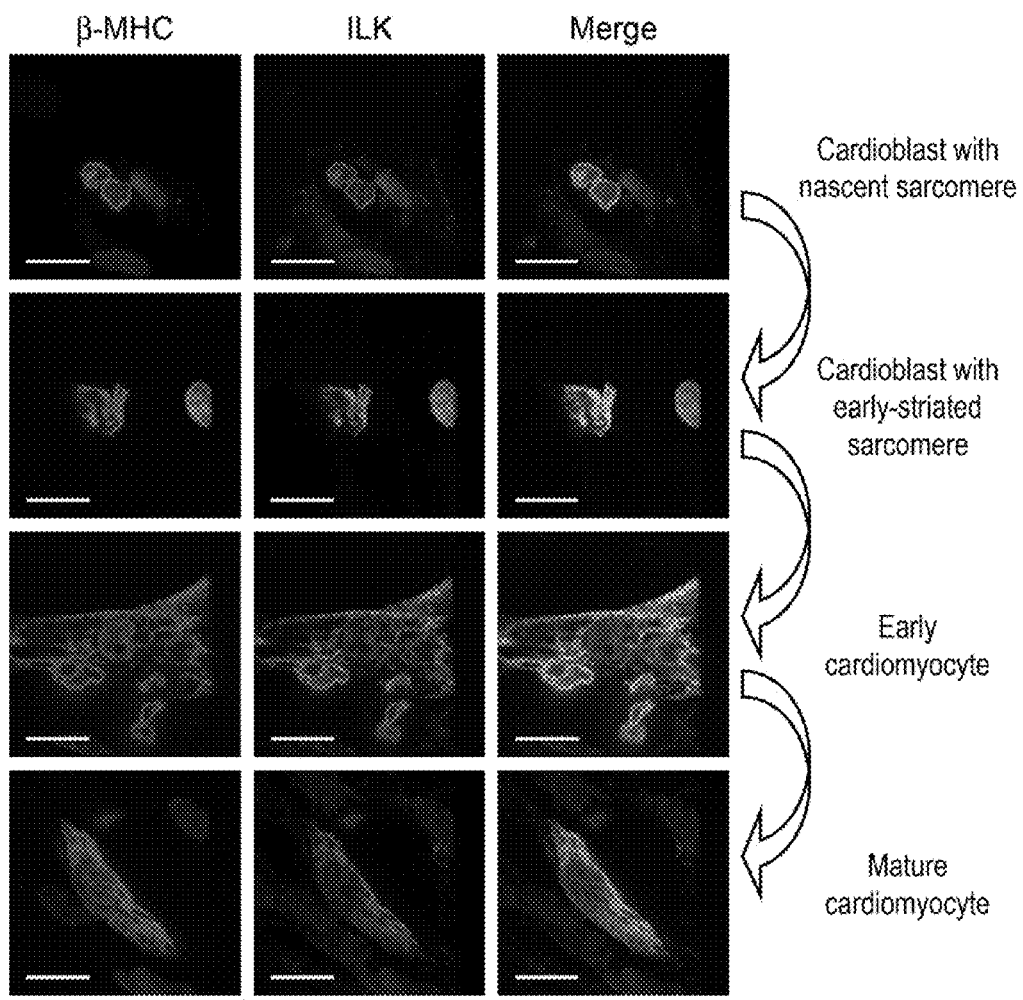
FIG. 5 provides a series of fluorescent confocal microscopy images of primary cultures of fetal myocardium-derived cells demonstrating that ILK expression can be detected in cells representing all stages of cardioblastic-to-cardiomyocytic differentiation with the human fetal heart derived cells (22 weeks gestation) cultured for 2 days and double immunostained with anti-β-MHC (MF-20) (red) and anti-ILK (green) antibodies and nuclei detected with DAPI staining (blue). Scale bar, 10 μm.

FIG. 5 shows that ILK promotes cardioblast maturation and that ILK co-localizes with β-MHC in sarcomeres of fetal cardiac cells. Confocal microscopy of primary cultures of fetal heart-derived cells immunostained with anti-β-MHC and anti-ILK antibodies revealed that both antigens invariably overlap in the cytoplasm of cells displaying different stages of cardiomyocytic differentiation (FIG. 5). In non-treated control cultures most of the β-MHC positive cells were early cardioblasts exhibiting nascent sarcomeric structures. Fewer cells displayed primitively striated sarcomeres that could be characterized as early cardiomyocytes and only occasional cells represented fully differentiated cardiomyocytes containing well-developed striated sarcomeres. The co-localization of ILK with sarcomeric β-MHC throughout progressive stages of human cardiomyocyte differentiation indicates a role for ILK in the morphogenesis of functional sarcomeres.

Figure 6A:
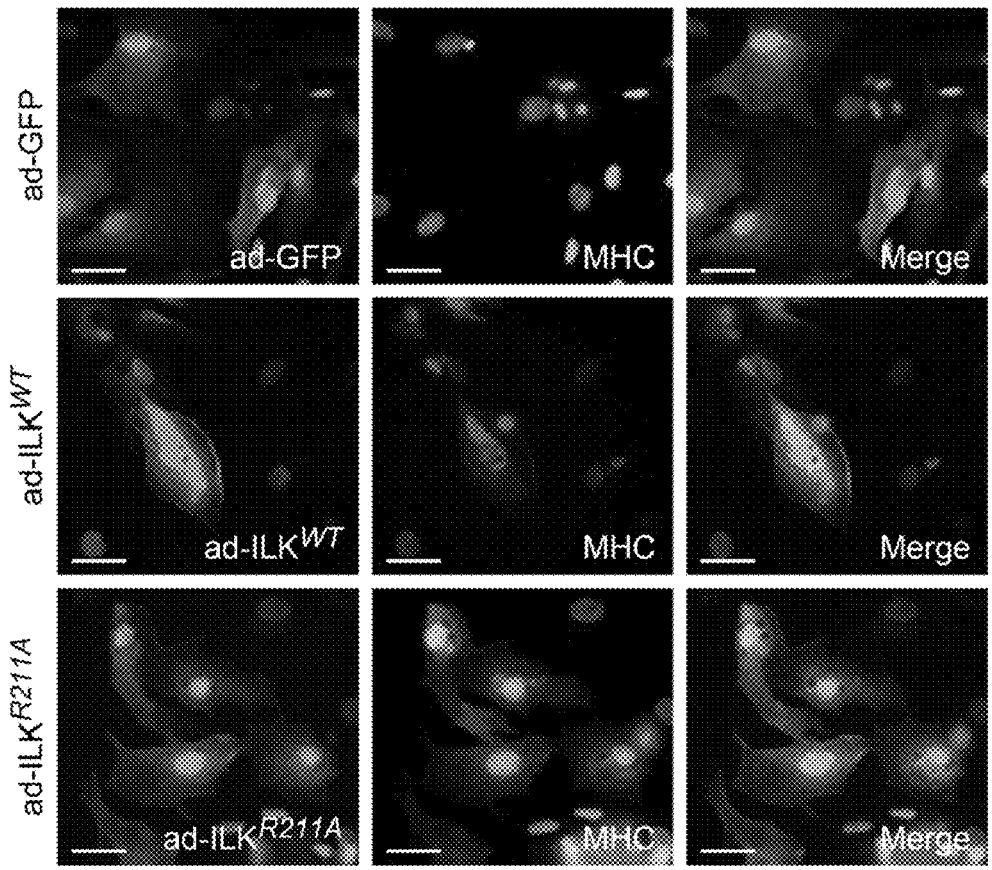
FIG. 6A provides a set of immunofluorescent images of ad-ILK$^{WT}$, ad-ILK_R211A and ad-GFP infected cells stained for β-MHC (red) and nuclei with DAPI (blue) in human fetal heart-derived cells (21 weeks gestation) with ad-ILK_R211A-transduced cultures demonstrating more β-MHC-positive cells than ad-ILK$^{WT}$-transduced counterparts. Scale bar, 30 μm.
Figure 6B:
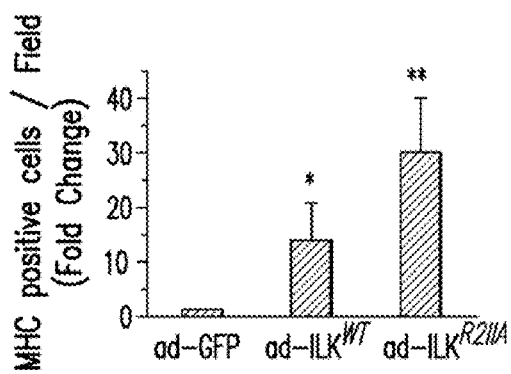
FIG. 6B is a bar graph showing quantification of the number of MHC positive cells detected by immunostaining in adherent fetal cardiomyocytes infected with adenovirus encoding ad-ILK$^{WT}$, ad-ILK_R211A and ad-GFP with mean values±SD, n=14 (random fields), *p<0.02, **p<0.001.
Figure 6C:
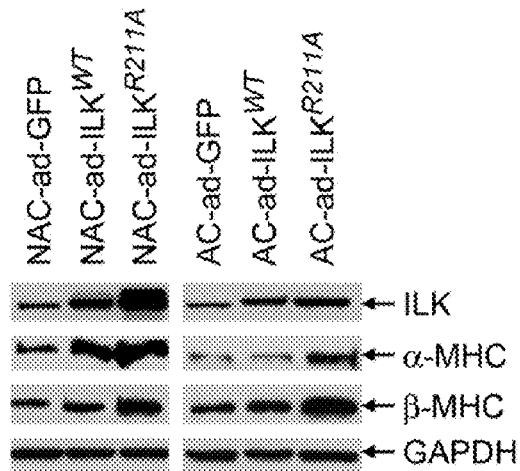
FIG. 6C is a set of images of Western blots for detecting ILK, cardiacspecific α-MHC and β-MHC expression levels in adherent (AC) and non-adherent (NAC) fetal cardiac fractions infected with ad-ILK$^{WT}$, ad-ILK_R211A and ad-GFP with each experiment performed at least three times on independent samples but with only one representative blot shown.

FIG. 6 shows that over-expression of ILK in human fetal cardiac cells induces production of MHC. A significant increase in the number of β-MHC-positive cells was observed in both ad-ILK$^{WT}$ (approximately 15-fold) and ad-ILK_R211A-transduced (approximately 30-fold) cultures compared to control cultures transduced with ad-GFP. Importantly, cells transduced with ad-ILK$^{WT}$ or ad-ILK_R211A vectors demonstrated similar co-localization of β-MHC and ILK proteins to that observed in non-infected cells, regardless of their stage of cardiomyocytic differentiation (FIG. 6A). Further, increasing expression levels of ILK in ad-ILK$^{WT}$ and ad-ILK_R211A cultures coincided with a proportional increase in number of β-MHC positive cells (WT, $p<0.021$; R211A, $p<0.001$) (FIG. 6B) and with the total amount of MHC protein detected by Western blot analysis with antibodies recognizing α- and β-chains of MHC (FIG. 6C), consistent with a dosage-dependent effect of ILK in stimulating cardiac sarcomeric formation. The levels of α-MHC and β-MHC in the ad-ILK$^{WT}$- and ad-ILK_R211A-transduced cultures exceeded levels of these cardiomyocyte markers detected in control cultures transduced with ad-GFP.

The LIM-homeodomain transcription factor Isl1 demarcates a distinct cardiac lineage referred to as the second heart field (see, e.g., Brade T et al., "The amphibian second heart field: Xenopus islet-1 is required for cardiovascular development," Dev Biol, 311(2):297-310 (2007), the entire contents and disclosure of which are hereby incorporated by reference), and has been implicated as part of an early transcriptional network which commits a cardiac fate in mesodermal cells. See, e.g., Anton R et al., "A molecular signature for the 'master' heart cell," Bioessays 29(5):422-426 (2007); and Lin L et al., "Beta-catenin directly regulates Islet1 expression in cardiovascular progenitors and is required for multiple aspects of cardiogenesis," PNAS USA 104(22):9313-9318 (2007), the entire contents and disclosure of which are hereby incorporated by reference. Loss-of function studies have confirmed the requirement for the expansion and survival of Isl1 cardiac precursors in mouse embryonic and human neonatal hearts in vivo. See, e.g., Oloumi A et al., "Regulation of E-cadherin expression and beta-catenin/Tcf transcriptional activity by the integrin-linked kinase," Biochim Biophys Acta 1691(1):1-15 (2004), the entire contents and disclosure of which are hereby incorporated by reference.

Figure 7A:
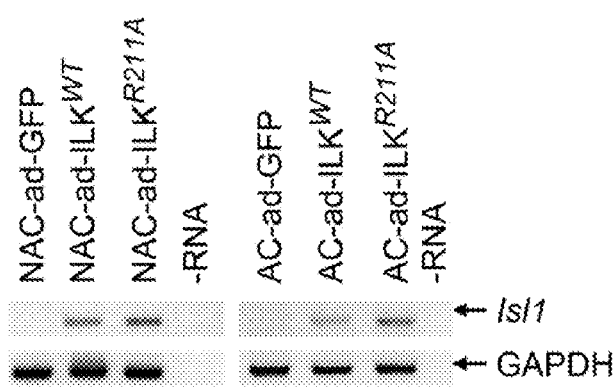
FIG. 7A is a set of images of (A) Semi-quantitative RT-PCR analysis showing Isl1 expression in adherent (AC) and non adherent (NAC) cells derived from fetal myocardium transduced with ad-ILK$^{WT}$, ad-ILK_R211A or ad-GFP. GAPDH expression was also measured in all experimental groups.

While ILK treatment is shown to increase the number of cardioblasts in vitro, it remains unclear whether ILK specifies a cardiomyocyte fate among uncommitted mesodermal cells or whether ILK induces proliferation of existing cardioblasts. To distinguish these possibilities, Isl1 expression was determined using RT-PCR in both adherent and non-adherent human fetal cellular fractions transduced with ad-ILK$^{WT}$, ad-ILK R211A and ad-GFP control. Results of these experiments revealed induction of Isl1 expression only in ad-ILK$^{WT}$ and ad-ILK_R211A cultures, but not GFP control-treated cells (FIG. 7A). This suggests that over-expression of ILK is crucial for initiating the early cardioblastic commitment of cardiac-resident mesodermal precursor cells.

Figures 7B, 7C:
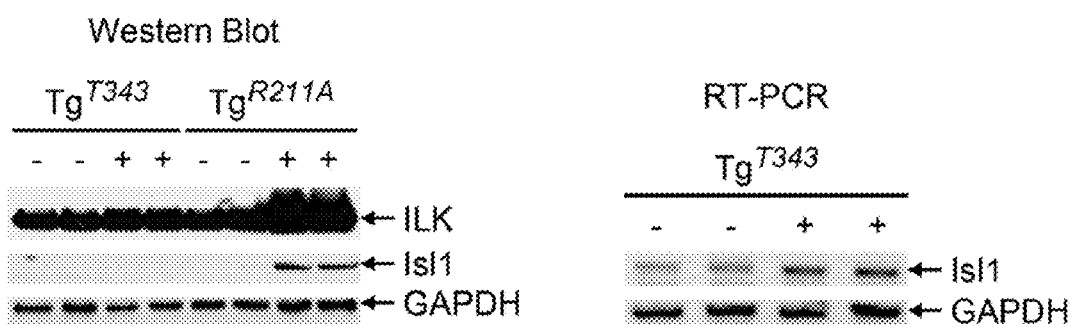
FIG. 7B shows images of Western blots of ILK and Isl1 in myocardial lysates derived from transgenic mice with cardiac-restricted expression of constitutively active ILK (Tg-ILK$^{S343D}$) or mutant ILK (Tg-ILK$^{R211A}$) and their littermate controls.
FIG. 7C shows images of blots for semi-quantitative RT-PCR analysis demonstrating increased Isl1 expression in hearts of transgenic mice with cardiac-restricted expression of constitutively active ILK (Tg-ILK$^{S343D}$) (+) compared to littermate controls (−).

To further address this claim, the protein levels of Isl1 were assayed by Western blot analysis of ventricular lysates from transgenic mice with cardiac-restricted expression of constitutively active ILK (ILK$^{S343D}$) or mutant ILK (ILK$^{R211A}$). See, e.g., Lu, H et al., (2006), supra. It was demonstrated that the protein levels of Isl1 in ILK$^{R211A}$ transgenic mice are markedly higher than in littermate controls (FIG. 7B). The expression levels of Isl1 in the ILK$^{S343D}$ genotype were undetectable by Western blot. However, RT-PCR analysis revealed higher Isl1 mRNA expression in the hearts of ILK$^{S343D}$ than in littermate controls, indicative of a positive correlation between ILK expression and that of Isl1 (FIG. 7C).

Figure 7D:
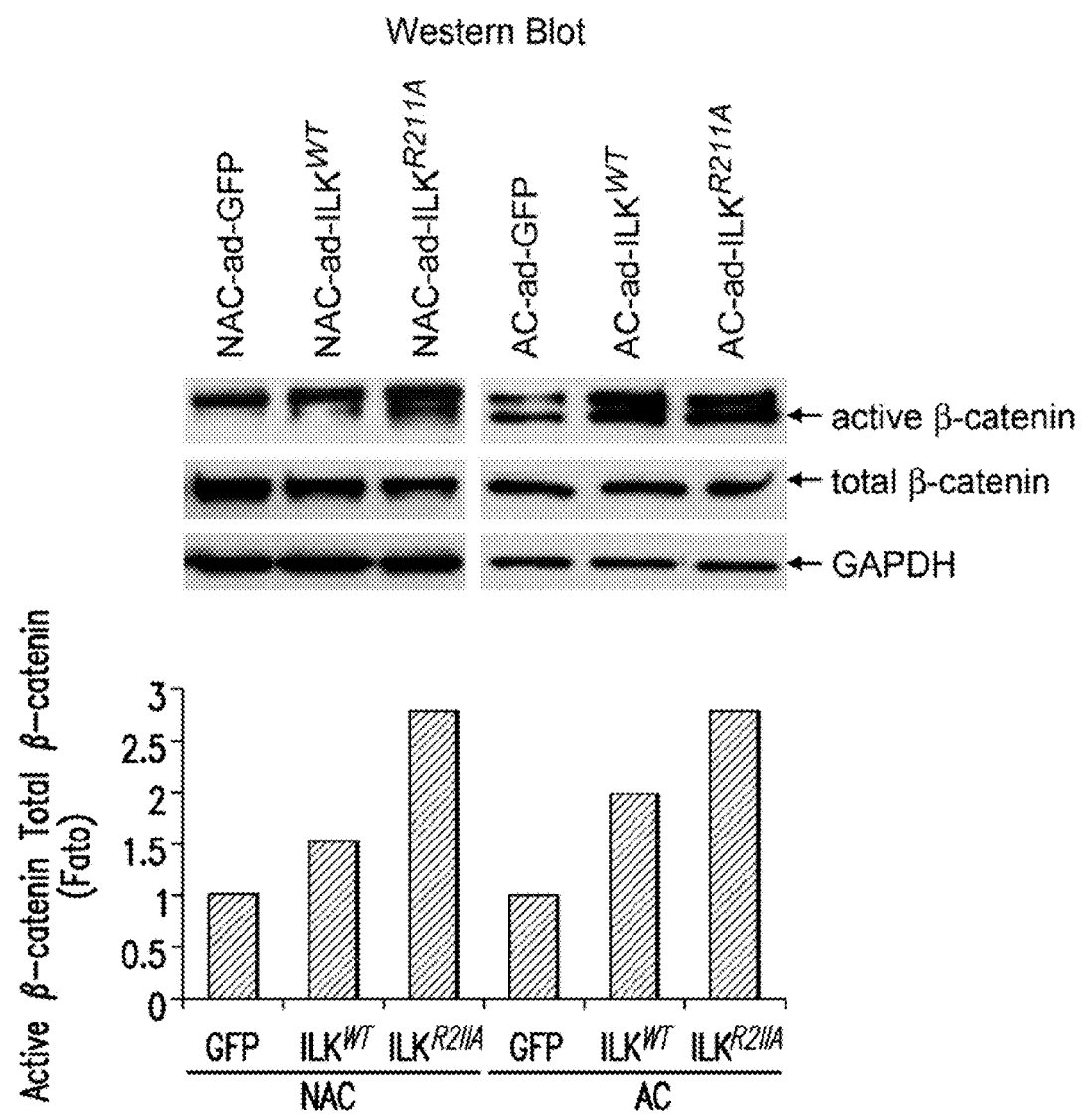
FIG. 7D shows images of Western blots (upper panel) showing the protein levels of stabilized, dephosphorylated β-catenin and total amount of β-catenin in adherent and non adherent fetal cardiac fractions infected with ad-ILK$^{WT}$, ad-ILK_R211A or ad-GFP. Films were scanned, and the fold increase in stabilization of active, dephosphorylated form of β-catenin relative to the total amount of β-catenin presented in a bar chart (lower panel). Each experiment was performed at least three times on independent samples with one representative blot shown.

Since activation of ILK regulates the stabilization and nuclear translocation of β-catenin in diverse cell types (see, e.g., Kirby M L et al., Cardiac Development. New York, N.Y.: Oxford University Press, 2007, Page 207) and β-catenin is required for Isl1 expression in cardiac progenitor cells and directly regulates the Isl1 promoter (see, e.g., Oloumi A et al., "Regulation of E-cadherin expression and beta-catenin/Tcf transcriptional activity by the integrin-linked kinase," Biochim Biophys Acta 1691(1):1-15 (2004), the entire contents and disclosure of which are hereby incorporated by reference), it was also tested whether over-expression of ILK in cultured fetal myocardial cells would correlate with stabilization of β-catenin. Overexpression of ILK is shown in these experiments to induce β-catenin stabilization in vitro and in vivo. As shown in FIG. 7D, the expression level of the stabilized (dephosphorylated) form of β-catenin was markedly increased both in ad-ILK$^{WT}$- and ad-ILK_R211A-transduced cultures, as compared to control ad-GFP infected cells ($P<0.001$; ILK_R211A vs ILK$^{WT}$ vs controls). This demonstrates that ILK regulates Isl1 expression through activation of β-catenin in human fetal cardiomyocytes. This phenomenon is observed in both the adherent and cardiomyocyte-enriched non-adherent cell fractions. Concordantly, the expression levels of β-catenin were significantly higher in ILK transgenic mouse hearts (ILK$^{R211A}$>ILK$^{S343D}$>littermate controls; P[ANOVA] $<0.001$; data not shown).

Figure 8:
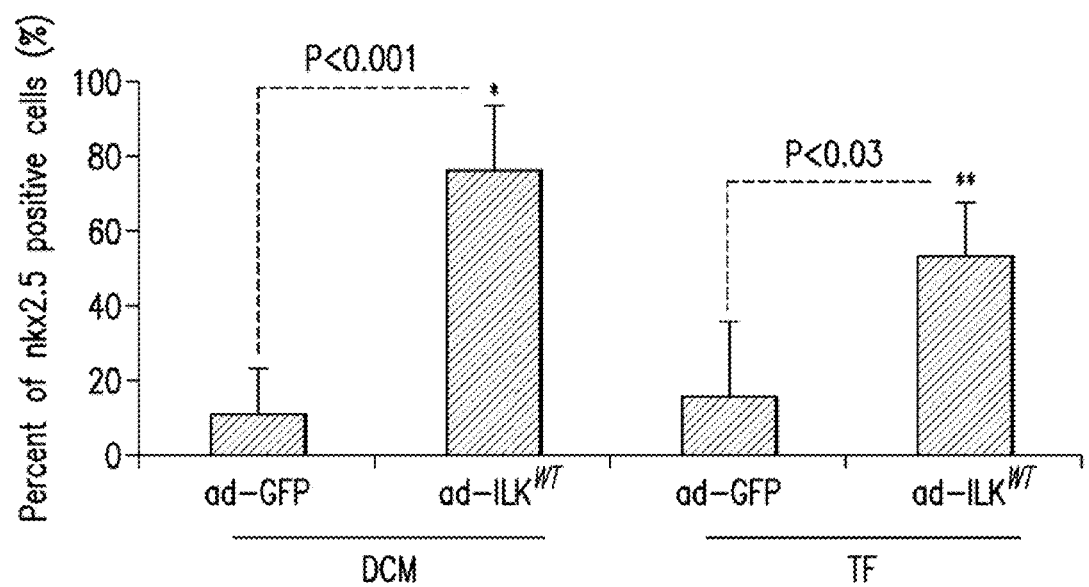
FIG. 8 shows quantitative immune-histochemistry of nkx2.5 positive cells using anti-nkx2.5 antibody showing that over-expression of ILK in primary cultures of cells isolated from myocardium of 17 year-old patient with advanced dilated cardiomyopathy (DCM) and from a 10 month-old child with tetralogy of fallot (TF) induced a significant increase in the number of nkx2.5 positive cells with cultures derived from both cases transduced with adenoviral vectors encoding human ad-ILK$^{WT}$ or empty virus ad-GFP. Bar graphs represent mean values±SD, n=10 (random fields).

Nkx2.5 is the primordial transcription factor required for cardiac gene expression and is specifically essential for left ventricular development. See, e.g., Kirby M L. Cardiac Development. New York, N.Y.: Oxford University Press (2007), Page 44, the contents and disclosure of which is hereby incorporated by reference. To test whether this cardiomyogenic target can be reactivated in postnatal myocardium of the diseased heart, freshly isolated cardiac cells from one 10 month-old child undergoing surgical correction of TF and from one 17 year-old patient with DCM requiring cardiac transplantation were analyzed. Both patient cell cultures were subjected to adenoviral over-expression of wild type ILK as described for the human fetal model. Adenoviral over-expression of ILK in primary cultures of cells isolated from myocardium of a patient with TF and from a patient with advanced DCM caused an increase in number of cells expressing nkx2.5. Ad-ILK$^{WT}$ transduction caused a large magnitude increase in the number of nkx2.5-positive cells based on multiple measurements in both disease phenotypes (FIG. 8).

Example 1

Discussion

Data presented herein indicates that experimental over-expression of the multifunctional serine/threonine kinase ILK in cultures of myocardial cells derived from human fetal heart leads to differentiation of a resident mesodermal precursor cell toward a primitive cardioblast phenotype and to the enhancement of further cardiomyocytic maturation. Proliferation and cellular hypertrophy of existing cardioblasts have been inferred as mechanisms accounting for somatic growth of the fetal heart at a stage after septation. See, e.g., Ieda, M et al., (2009), supra; and Urbanek K et al., "Stem cell niches in the adult mouse heart," *PNAS USA* 103(24):9226-9231 (2006), the entire contents and disclosure of which are hereby incorporated by reference. However, the striking finding herein that high frequency cardiomyocyte specification is inducible by over-expression of ILK at a stage subsequent to definitive ventricular chamber formation indicates the persistence of a recruitable precursor cell population late in human cardiac development. Importantly, it is also demonstrated that experimental over-expression of ILK increases the frequency of cardiomyogenic differentiation in cultures of myocardial cells derived from diseased hearts of patients with TF and DCM. These results are consistent with reports that cardiac resident progenitor cells in the adult murine (see, e.g., Urbanek K et al., "Myocardial regeneration by activation of multipotent cardiac stem cells in ischemic heart failure," *PNAS USA* 102(24):8692-8697 (2005), the entire contents and disclosure of which are hereby incorporated by reference) and human (see, e.g., Smith RR et al., "Regenerative potential of cardiosphere-derived cells expanded from percutaneous endomyocardial biopsy specimens," *Circulation*, 115(7):896-908 (2007); and Rochais F et al., "Signaling pathways controlling second heart field development," *Circ Res*, 104(8):933-942 (2009), the entire contents and disclosure of which are hereby incorporated by reference) hearts may be activated and reenter a normal nkx2.5-regulated developmental pathway in response to injury. Support for a critical role of ILK in the initiation and maintenance of the normal cardiogenic phenotype is also endorsed by studies showing that disruption of ILK signaling leads to neonatal cardiomyopathy. See, e.g., Bendig, G et al., (2006), supra; and White, D E et al., (2006), supra.

ILK-induced fetal myocardial cells exhibited a spectrum of progressive differentiation. Early cardioblasts displayed nascent sarcomeric structures and were nkx2.5-positive indicative of a cardiomyocytic specification. Interestingly, a population of early presumptive cardioblasts displayed coexistence of intracellular collagen fibrils and nascent sarcomeres, possibly indicating their origin from progenitors with both fibroblastic and cardiomycytic potential. The adherent cellular fraction is typically depleted in many studies by preplating cells for the purpose of yielding cardiomyocyte-enriched cultures. See, e.g., Buckingham, M et al., "Building the mammalian heart from two sources of myocardial cells," *Nat Rev Genet* 6(11):826-835 (2005), the entire contents and disclosure of which are hereby incorporated by reference. However, it is revealed herein that the adherent fraction is a source of cardiac progenitor cells capable of differentiation into a cardiomyocytic phenotype.

Cells exhibiting progressively more distinct striations typical of differentiated cardioblasts were mostly present in non-adherent aggregates and stained positively for cardiac-specific sarcomeric proteins. Moreover, confocal microscopy revealed localization of ILK to sarcomeres suggesting a possible role for ILK in nucleating new sarcomeres, and providing a basis for the pro-hypertrophic effects observed with ILK activation. See, e.g., Lu H et al., (2006), supra. Localization of ILK to sarcomeric structures was reported in fully developed cardiomyocytes in zebrafish. See, e.g., Bendig, G et al., (2006), supra.

The results herein demonstrate that ILK-induced cardiomyogenesis coincided with β-catenin activation, and is consistent with previously published results showing that activation of Wnt/β-catenin pathway enhances embryonic stem cell differentiation into cardiomyocytes (see, e.g., Naito, A T et al., (2006), supra), and accelerates cardiogenesis in the undifferentiated P19CL6 cell line. See, e.g., Durbin A D et al., "JNK1 determines the oncogenic or tumor-suppressive activity of the integrin-linked kinase in human rhabdomyosarcoma," *J Clin Invest*, 119(6):1558-1570 (2009), the entire contents and siclosure of which are hereby incorporated by reference. Other studies indicate more complex context-specific and antagonistic effects of Wnt signaling on cardiomyogensis. See, e.g., Qyang Y et al., (2007), supra; and Naito A T et al., (2006), supra. ILK can also signal through a c-Jun-N-terminal kinase (JNK/c-Jun) signaling axis independently of the canonical signaling target GSK-3β. See, e.g., Flaherty M P et al., "Noncanonical Wnt11 signaling is sufficient to induce cardiomyogenic differentiation in unfractionated bone marrow mononuclear cells," *Circulation*, 117(17):2241-2252 (2008), the entire contents and disclosure of which are hereby incorporated by reference. Since non-canonical Wnt signaling via Wnt11 is sufficient to induce cardiomyogenesis in bone marrow mononuclear cells in a JNK/c-Jun-dependent manner (see, e.g., Easley C A B-Y A et al., "Expression of constitutively active P70 S6K, a protein translation mediator, induces differentiation in pluripotenet human embryonic stem cells," Presentation at the 2009 7th Annual Meeting of the International Society for Stem Cell Research), the myogenic effects of ILK may depend upon the contextual balance of canonical and non-canonical Wnt signaling. It has been shown that ILK elevates the protein translation mediator p70 S6 kinase (p70S6K) during cardiac hypertrophy (see, e.g., Lu H, et al., (2006), supra), and independently that p70S6K induces differentiation in human embryonic stem cells. See, e.g., Stpyridis M P C B et al., "Retinoic acid orchestrates biphasisc FGF/ERK 1/2 signalling to promote mouse embyonic stem cell differentiation," Presentation at the 2009 7th Annual Meeting of the International Society for Stem Cell Research. The results herein indicating the efficacy of ILK_R211A, which is deficient in agonist-inducible PI3K signaling, in promoting cardiogenesis suggest that intracellular ILK over-expression may act as a universal growth factor signal to enhance differentiation in susceptible precursor cells.

ILK over-expression is shown herein to increase the expression of the early nodal marker of cardiogenesis, Isl1, in human cardiac cells in vitro and in the ILK transgenic mouse heart in vivo. Isl1 may be expressed in first heart field (FHF) as well as the secondary heart field and thus represent a pan-cardiocytic marker for both myocardial cell lineages (see, e.g., Liu Z et al., "WNT signaling promotes Nkx2.5 expression and early cardiomyogenesis via downregulation of Hdac1," *Biochim Biophys Acta*, 1793(2):300-311 (2009); and Laugwitz K L et al., "Islet1 cardiovascular progenitors: a single source for heart lineages?" *Development*, 135(2):193-205 (2008), the entire contents and disclosures of which are hereby incorporated by reference), which may account for the finding herein of ILK-induced Isl1 expression in human fetal cells that are assumed to derive predominantly from the FHF-derived ventricular mass.

It is shown herein that activation of a multi-functional kinase, in distinction to the effects of certain growth factors, can lead to new cardiomyogenesis in the human fetal heart. Importantly, the capacity for stimulation of new formation of nkx2.5-positive cardioblasts was also shown in cardiac cells derived from postnatal diseased hearts, thus highlighting the ability of ILK to activate latent regenerative pathways even in advanced cardiac diseases. The results herein indicate that ILK may be a critical component of the mechanisms responsible for the induction of net cardiomyogenesis among the diversified population of cells comprising the human heart. The data herein encourages future studies aimed at controlled activation of the ILK pathway that may be useful in promoting cardiomyocytic differentiation of induced pluripotent cells and eventually lead to the development of novel therapeutic approaches allowing regeneration of diseased human myocardium.

Example 2

Mutation in Integrin-Linked Kinase (ILK_R211A) is Cardioprotective

Integrin-linked kinase (ILK) is a multidomain integrin adaptor protein that possesses widely conserved structural and signal transduction functions. See, e.g., McDonald P C et al., (2008), supra. ILK has been implicated as both a cardioprotective (see, e.g., Lu H et al., (2006), supra; and Hannigan G E et al., (2007), supra) and oncogenic (see, e.g., Hannigan G et al., (2005), supra and Durbin, A D et al., (2009), supra) target so that the contextual regulation of ILK is therapeutically important but so far unresolved. It is shown herein that the transgenic mouse heart over-expressing an activation-resistant form of ILK deficient in membrane phosphatidylinositol (3,4,5)-trisphosphate (PIP3) binding ($ILK^{R211A}$) exhibited a highly cardioprotective phenotype that exceeded that of the constitutively-active ILK mutant ($ILK^{S343D}$). Microarray analysis revealed upregulation of heat shock protein 70 complex (Hsp70) message in the R211A mutant expressing transgenic heart. Immunoprecipitation studies in transgenic mouse hearts, and in mouse and human cardiac cell cultures adenovirally infected with the corresponding ILK mutations in vitro, confirmed upregulation and specific binding of ILK point mutant proteins to Hsc70/Hsp70 that was greatest with ILK_R211A mutant protein. These findings show that mutation of the conserved ILK induces Hsp70 binding that serves to stabilize and enhance its expression levels and function. ILK_R211A is shown herein to be cardioprotective but, unlike most cytoprotective strategies, is predicted to be non-oncogenic. See, e.g., Persad, S et al., (2001), supra. These results introduce a novel target discovery theme in which kinase mutations can be engineered to optimize cardioprotective effects, while minimizing potential oncogenicity.

Example 2

Introduction

ILK binds to cytoplasmic domains of β1-, β2-, and β3-integrin subunits and nucleates a supramolecular complex at the site of focal adhesions that connects to the actin cytoskeleton, thereby linking the extracellular matrix to the cytoskeleton in a manner essential for bidirectional force transduction. See, e.g., Legate, K R et al., J Cell Sci (2009), supra. Adaptor complexes centered around ILK comprise a signaling platform that, in response to distinct signal inputs from integrins and growth factor receptor tyrosine kinases (RTKs), activate signaling pathways regulating growth, survival, cell cycle progression, epithelial-mesenchymal transition, and cellular differentiation. See, e.g., Hannigan, G et al., (2005), supra; and Legate K R et al., Genes Dev (2009), supra. ILK activation by growth factor stimulation is normally regulated in a PI3K-dependent manner involving activation of ILK by phosphatidylinositol (3,4,5)-trisphosphate (PIP3), thought to involve interaction with the central pleckstrin homology (PH)-like domain of ILK. See, e.g., Delcommenne M et al., (2008), supra. Canonical ILK signaling induces downstream phosphorylation of Akt/PKB on Ser473 and glycogen synthase-3β (GSK-3β) on Ser9, which may provide a molecular basis for its prosurvival, prohypertrophic effects. See, e.g., Lu H et al., (2006), supra; Hannigan G E et al., (2007), supra; and White, D E et al., (2006), supra.

Hypoxia is a potent signal inherent in diverse pathological processes affecting most organ systems, but especially in the heart where ischemia and infarction are both prominent features of many cardiac diseases. To test the cardioprotective properties of ILK and to investigate putative mechanistic pathways, LAD ligation was performed in two distinct transgenic ILK-overexpressing mouse models. One model uses a constitutively-active serine (S) to aspartic acid (D) substitution in the putative autophosphorylaton site of the human ILK gene ($ILK^{S343D}$) (see, e.g., Wickstrom S A et al., "The ILK/PINCH/parvin complex: the kinase is dead, long live the pseudokinase!" EMBO J 29(2):281-291 (2009). The other model uses a mutant ILK gene deficient in membrane PIP3 binding as a result of an arginine (R) to alanine (A) point mutation of the PH domain of ILK ($ILK^{R211A}$) that impairs membrane PIP3 binding and renders it resistant to receptor-mediated activation, thus neutralizing the potentially oncogenic properties of the native ILK molecule. See, e.g., Persad, S et al., (2001); and Delcommenne M et al., (2008), supra.

Example 2

Methods

Generation of Transgenic Mice. The methods for generation of transgenic animals conveying cardiac-specific over-expression of wild type ($ILK^{WT}$) and mutant ($ILK^{R211A}$; $ILK^{S343D}$) versions of human wild type ILK gene have been previously described. See, e.g., Lu H et al., (2006), supra. The methods used for adenoviral infection of human wild type and $ILK^{R211A}$ constructs into murine and human myocardial-derived cardiac cells, immunofluoresence imaging and Western blot analyses were performed as described. See, e.g., Lu H et al., (2006), supra; and Yamabi, H et al., (2006), supra. Statistical comparison of ILK-specific effects relied on a paired t test or analysis of variance (ANOVA) followed by the multiple-comparison Bonferroni t test to assess differences among groups. The significance level was set at P<0.05.

Research Ethics Board Approval. The acquisition of human heart samples was approved by an institutional review committee and all subjects gave informed consent to the study. Regarding mouse studies, The Animal Care Committee at the Hospital for Sick Children, which operates in accordance with the Terms of Reference following the Canadian Council on Animal Care Guidelines and federal and provincial regulations/legislations, gave approval to this study.

Microarray analysis using Affymetrix GeneChip Hybridization. Experimental design, gene lists, hierarchical trees, chip hybridizations, and statistical analyses were done in compliance with the Minimum Information About a Microarray Experiment (MIAME) guidelines. See, e.g., Brazma A et al., "Minimum information about a microarray experiment (MIAME)-toward standards for microarray data," Nat Genet 29(4):365-71 (2001), the entire contents and disclosure of which are hereby incorporated by reference. Samples were prepared for hybridization according to standard Affymetrix instructions and performed at the Genomic Core Facility at the Hospital for Sick Children. Total RNA (TRNA) was isolated from 12 mouse heart samples utilizing Trizol Reagent (GIBCO/BRL) following the manufacturer's protocol. The quality of tRNA was assessed using the Agilent 2100 Bioanalyzer (version A.02.0151232, Agilent Technologies). Only RNA samples with the OD ratio of 1.99-2.0 at 260/280 were used for microarray analysis. A total of 12 hybridizations from four groups of mouse genotypes (S343D+, S343D−, R211A+, and R211A−) were performed using the Mouse MOE 430 2.0 array chip (Affymetrix). Cluster analysis and network mapping were performed using Gene Set Analysis in GeneSpring GX 11 (Agilent Technologies) and Partek Pro2000 platforms (Partek Inc., St. Louis, Mo.).

Mouse Echocardiography. Echocardiograms evaluating baseline systolic and diastolic function were performed in all mice under general anesthetic using a Vevo 660 UBM (VisualSonics, Toronto, ON, Canada) revealed no significant differences in heart rate, stroke volume, cardiac output, fractional shortening, left ventricular dimensions, or pulmonary venous flow patterns. See, e.g., Zhou Y Q et al., "Abnormal cardiac inflow patterns during postnatal development in a mouse model of Holt-Oram syndrome," *Am J Physiol Heart Circ Physiol* 289(3):H992-H1001 (2005); and Zhou Y Q et al., "Comprehensive transthoracic cardiac imaging in mice using ultrasound biomicroscopy with anatomical confirmation by magnetic resonance imaging," *Physiol Genomics* 18(2):232-44 (2004), the entire contents and disclosure of which are hereby incorporated by reference. A total of 53 mice underwent ligation of left anterior descending (LAD) coronary artery, including ILK$^{R211A}$ (n=13), ILK$^{S343D}$ (n=12) and respective littermate controls. Three mice died following surgery (one, ILK$^{R211A+}$; one, ILK$^{S343D+}$ and one, ILK$^{R211A−}$), which was not statistical different among genotypes (p=0.89).

Echocardiograms were then performed at 7 and 28 days following the LAD ligation. LV dimensions and ejection fraction (systolic and diastolic) were determined from the standard parasternal long axis M-mode view. Infarct size was measured by tracing the area of akinesis in the parasternal long axis view, and the area of synchronous contraction on the anterior border of the heart calculated, indicative of viable, non-infarcted myocardium. Differences among transgenic groups were evaluated using a paired analysis adjusting for baseline function and compared using ANOVA. Differences between groups were compared using linear contrasts (PROC GLM) in SAS 9.2 (Cary, N.C.).

Heart cell lysates from DCM patients. Hearts samples from the left ventricle from a heart with DCM at the time of cardiac transplantation. The samples were minced and washed with phosphate-buffered saline. Cells isolation was performed with 0.2% trypsin and 1 mg/ml type II collagenase in 0.02% glucose phosphate-buffered saline (PBS), pH7.4 solution at 37° C. After dissection, cells were incubated on plastic culture dishes (Sarstedt, Inc, Newton, N.C.) in Iscove modified Dulbecco medium (IMDM, Gibco, Invitrogene Corporation, Carlsbad, Calif.) containing penicillin and streptomycin and supplemented with 10% fetal bovine serum (FBS, Gibco). Cells were cultured to 60%-70% confluency prior to adenovirally mediated infection with ILK constructs containing green fluorescent protein (GFP), in replication-deficient serotype 5 adenovirus encoding either the human wild-type ILK gene incorporating GFP construct (ILK$^{WT}$) or ILK_R211A or an empty GFP virus construct (EV) or no intervention (C). Cells were infected at 37° C. at multiplicity of infection of 1.5 in IMDM with 10% FBS for 24 hours and analyzed 3-5 days after infection with or without passage. The infection efficiency was confirmed by more than 80% GFP positivity.

Example 2

Results

Figure 12A:
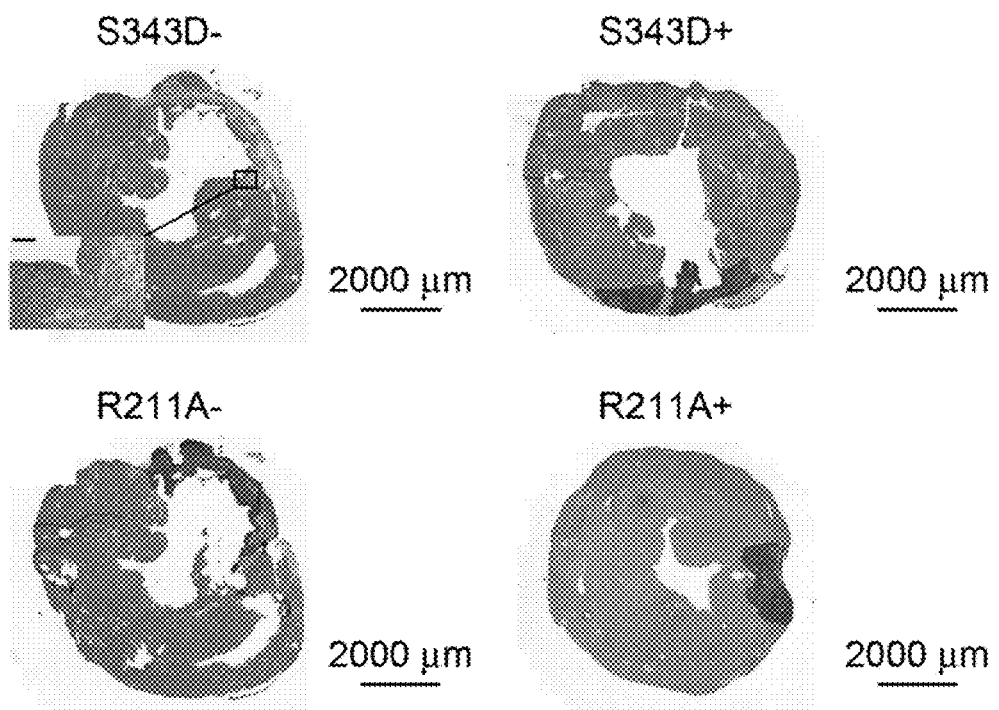
FIG. 12A is a set of images of H&E stained hearts from transgenic mice expressing ILK$^{R211A}$ or ILK$^{S343D}$ mutant proteins versus control following LAD ligation.
Figure 12B:
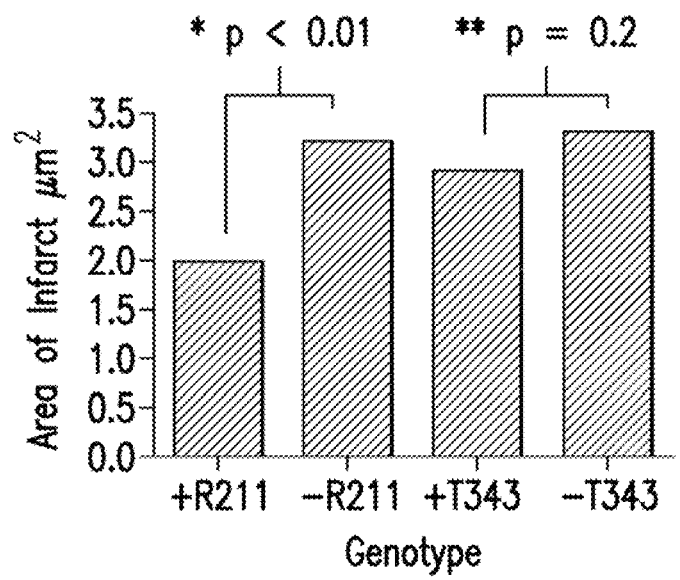
FIG. 12B is a bar graph of the area of infarct in hearts of transgenic mice expressing ILK$^{R211A}$ or ILK$^{S343D}$ mutant proteins versus control following LAD ligation.
Figure 12C:
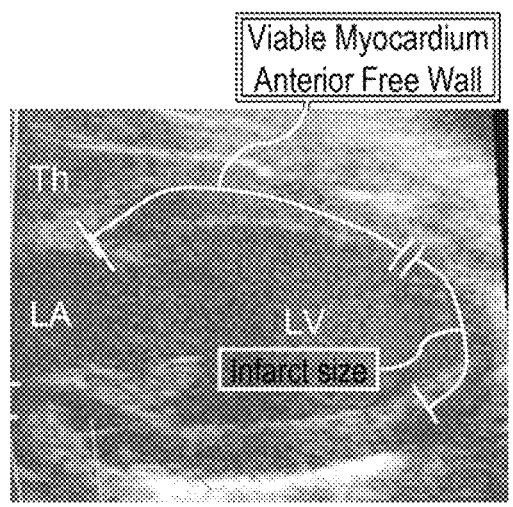
FIG. 12C is an image of an echocardiograph of a heart following LAD ligation illustrating the method used to calculate infarct size and reciprocally the amount of viable myocardium.
Figure 13A:
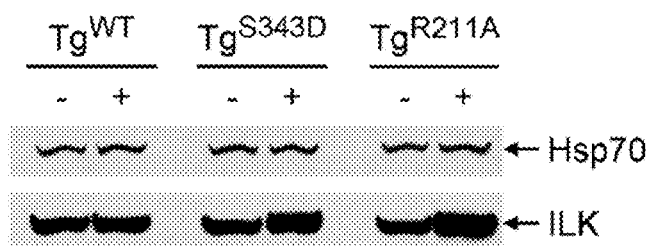
FIG. 13A is a Western blot showing the expression levels of ILK and Hsp70 in ventricular lysates of transgenic mice with wild type (WT) and mutant (S343D and R211A) ILK transgenes expressed under the promoter of the cardiac specific α-myosin heavy chain in comparison to littermate controls (−) indicating highest expression levels of ILK in ILK$^{R211A}$ Tg, with no differences in total levels of Hsp70 across genotypes.

Transgenic mice expressing the ILK$^{R211A}$ protein exhibited a cardioprotective phenotype against LAD ligation that was greater than that in mice expressing the activated ILK$^{S343D}$ mutant protein. Based upon echocardiographic measurements of akinetic LV wall motion determined at 28 day to allow post-infarct remodeling, ILK$^{R211A}$ sustained significantly smaller infarcts compared to littermate controls and to that of ILK$^{S343D}$ mice [p(ANOVA)<0.05 for both comparisons] (See FIGS. 10, 11, 12A, 12B, and 12C). Reduction in infarct size in the ILK$^{R211A}$ genotype was confirmed by planimetric measurement of H & E stained hearts (p=0.04) and by echocardiographic measurement of infarct size and reciprocally the amount of viable myocardium. (See FIGS. 12B and 12C). Enhanced cardioprotection in the ILK$^{R211A}$ genotype was also evident by an increase in stroke volume (p=0.04) and decrease in heart rate (p=0.02), consistent with better preservation of cardiac function (See FIG. 11). In contrast, the ILK$^{S343D}$ mouse exhibited non-significant trends towards a reduction in infarct size by echo (p=0.12) and by histological measurement (p=0.2). ILK expression levels correlated with the degree of infarct reduction and were highest with expression of the R211A mutant protein and intermediate with expression of the S343D mutant protein (See FIG. 13A).

To explore the mechanism through which the ILK$^{R211A}$ mutation conferred a higher expression level and a greater degree of cardioprotection, microarray analysis was performed in the transgenic heart. This confirmed that the ILK$^{R211A}$ mutation, and to a lesser degree, the activated S343D mutation, is associated with a robust heat shock mRNA response. ILK$^{R211A}$ hearts showed a dominant baseline pattern of upregulated of heat shock proteins (Hsps), featuring highest activation of Hsp70 (~3.4-fold) (See FIG. 9). More modest (1.3-fold) activation of Hsp70 was evident in ILK$^{S343D}$ mice (not shown). Network mapping performed to investigate potential ILK-regulated targets in ILK$^{R211A}$ hearts confirmed numerous interactions among ILK and Hsps including Hsp70 (not shown). In fact, 11 of 22 genes exhibiting significant upregulation (>1.5 fold) are GO classified heat-shock/stress-responsive genes). Interestingly, the only one gene showing significant downregulation was stub1 or the E3 ubiquitin ligase, CHIP (carboxyl terminus of Hsc70-interacting protein). Since CHIP promotes proteosomal degradation of a wide range of normal and misfolded proteins, its downregulation in ILK$^{R211A}$ Tg hearts would predict stabilization of ILK$^{R211A}$ protein as an Hsp70 client protein.

Figure 13B:
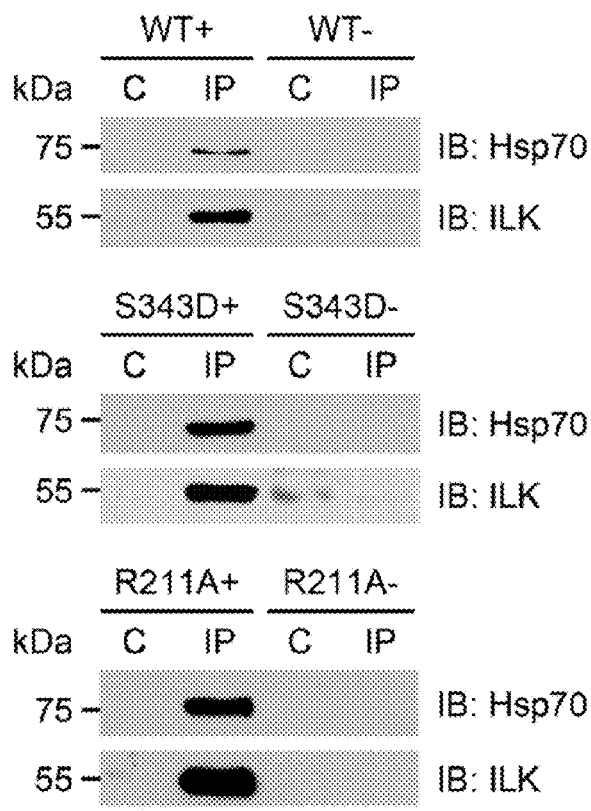
FIG. 13B is an image of an immunoblot of ventricular lysates of Tg mice expressing wild-type or mutant (S343D or R211A) ILK transgenes versus littermate controls immunoprecipitated with anti-ILK antibodies and immunoblotted with anti-ILK and anti-Hsp70 antibodies with results indicating a gradient of ILK binding to Hsp70 with the highest intensity with ILK$^{R211A}$, intermediate intensity with ILK$^{S343D}$, lowest in wild-type and absent in controls. Molecular mass marker positions are shown on the left.
Figure 13C:
FIG. 13C is an image of an immunoblot produced similarly as in FIG. 11B but for Hsp90 with no detectable binding between ILK_R211A and Hsp90.

To determine the mechanism underlying increased expression of the ILK$^{R211A}$ mutant protein, the capacity of ILK to bind various Hsps was tested in co-immunoprecipitation (Co-IP) assays using heart tissue derived from ILK$^{R211A}$, ILK$^{S343D}$, and control mice. Myocardial ILK expression levels were found to be the highest in ILK$^{R211A}$, lowest in the control, and intermediate in the ILK$^{S343D}$ genotype (See FIG. 13A). Co-IP studies revealed a gradient of Hsp70 binding to immunoprecipitated ILK mutations that was highest in ILK$^{R211A}$ transgenic hearts, intermediate in ILK$^{S343D}$ transgenic hearts, and not detectable in littermate control hearts (See FIG. 13B). To determine if Hsp70 binding resulted from mutation-induced protein misfolding, Co-IP was performed in hearts with transgenic over-expression of wild type (WT) ILK, which revealed minimal Hsp70 binding to immunoprecipitated WT ILK, indicating that Hsp70 binding was stimulated to a greater extent by the ILK mutations examined (See FIG. 13B). ILK$^{R211A}$ exhibited specific binding to Hsp70, but not Hsp90 (See FIG. 13C).

Figure 14A:
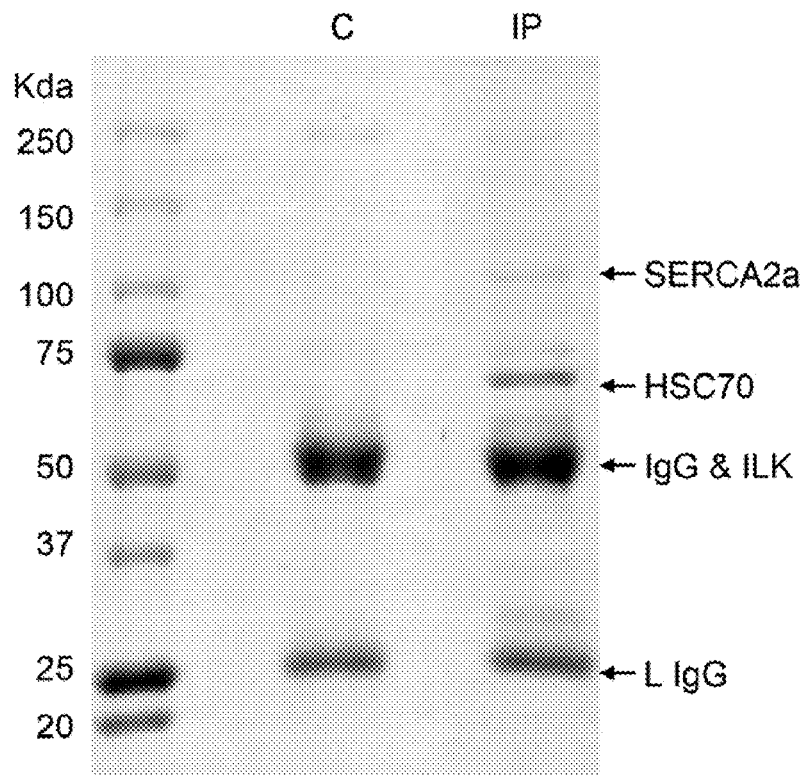
FIG. 14A is an image of a Coomassie stained gel with lysates prepared from transgenic mouse (ILK$^{R211A}$) hearts with (i) control lane (C) using protein A and rabbit IgG; and (ii) immunoprecipitation (IP) lane using ILK rabbit antibody and protein A, showing several new co-immunoprecipitated bands on the Coomassie Blue stained gel identified by mass spectroscopy (MS) as Hsc70 and SERCA2. (The IgG heavy chain band overlaps with that of ILK, and light chain IgG (LIgG) shown).
Figure 14B:
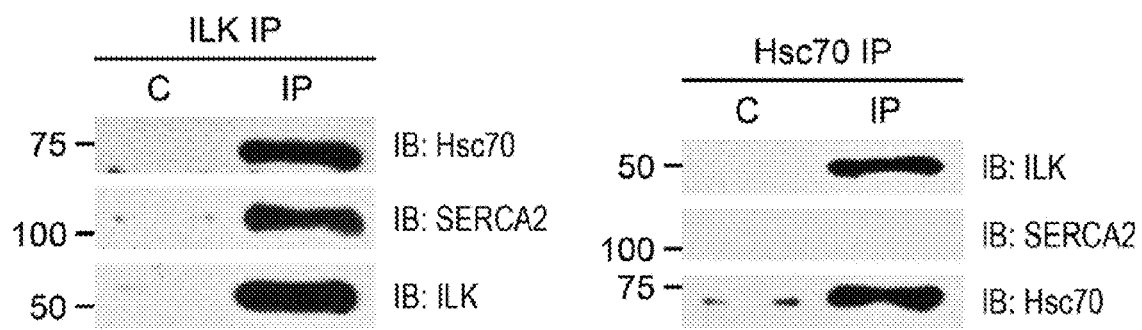
FIG. 14B is a set of images of immunoblots using lysates prepared from transgenic mouse (ILK$^{R211A}$) hearts immunoprecipitated with a rabbit anti-ILK antibody and protein A beads or with a rat anti-Hsc70 antibody and protein A beads. The control samples for ILK IP were immunoprecipitated with rabbit IgG and protein A beads. The control samples for Hsc70 IP were immunoprecipitated with rat IgG and protein A beads. The immunocomplexes for ILK IP were analyzed by immunoblot with mouse ILK antibody, rat Hsc70 antibody, and goat SERCA2 antibody with the immunocomplexes for Hsc70 IP analyzed by immunoblot with rabbit ILK antibody, goat SERCA2 antibody (SERCA; sc-8095; Santa Cruz Biotechnology Inc.) and mouse Hsp70 antibody (Hsp70; sc-32239; Santa Cruz). C, control; IP, ILK IP or Hsp70 IP or co-IP; and IB, immunoblot, respectively. All the results were repeated at least 3 times.

Potential ILK-interacting proteins were investigated using Coomassie staining of SDS gels performed on ILK immunoprecipitates derived from ILK$^{R211A}$ mouse hearts (See FIGS. 14A and 14B). This analysis revealed two major new bands which were identified using the LTQ XL* Linear Ion Trap Mass Spectrometer (Thermo Fischer Scientific); one was identified as heat-shock cognate protein (Hsc70, also known as Hsp73). The binding of ILK to Hsc70 is demonstrated in Co-IP analysis using a monoclonal antibody that specifically recognizes Hsc70 confirming that Hsc70 is the major Hsp70 chaperone that binds to the ILK$^{R211A}$ protein. (See FIG. 14B) Hsc70 has been shown to promote proper refolding and preserved function of denatured luciferase in concert with the canonical DnaJ/Hsp40 chaperone Dnaj1 which accords well with our microarray results indicating upregulation of Hsc70 and Dnaj1 in the ILK$^{R211A}$ genotype. See, e.g., Terada K et al., "Multiple molecules of Hsc70 and a dimer of DjA1 independently bind to an unfolded protein," *J Biol Chem* 285(22): 16789-16797 (2010), the entire contents and disclosure of which is hereby incorporated by reference.

Figure 15:
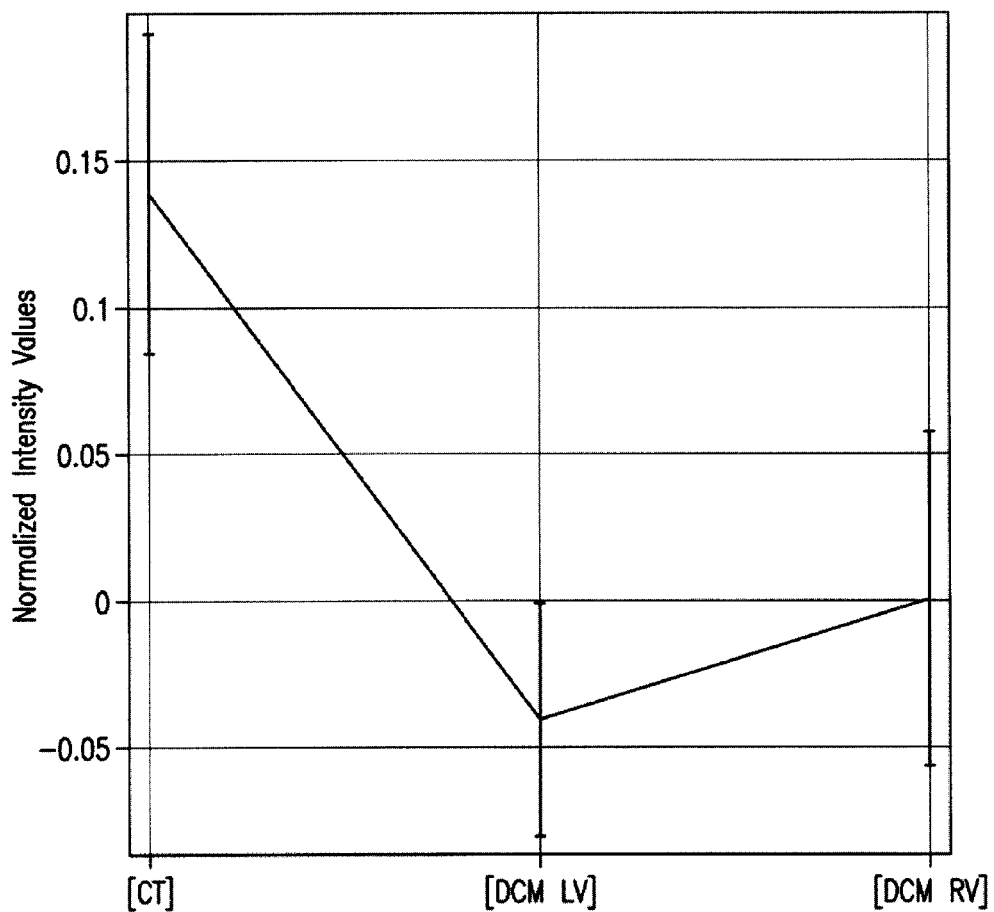
FIG. 15 is a line graph showing ILK mRNA Expression Levels in Human Dilated Cardiomyopathy (DCM) with total RNA (TRNA) isolated from samples derived from the right (RV) and left (LV) ventricles of patients with DCM, and as control, from the RV of patients undergoing surgical closure of ventricular septal defects with normal ventricular function (C), utilizing Trizol Reagent (GIBCO/BRL) following the manufacturer's protocol. The quality of TRNA was assessed by Agilent 2100 Bioanalyzer (version A.02.0151232, Agilent Technologies). Microarray analysis was performed on 17 samples representing 6 separate patients using the GeneChip® Human Gene 1.0 ST Array (Affymetrix). Analysis of ILK expression levels was performed using GeneSpring 11 (Agilent).
Figure 16A:
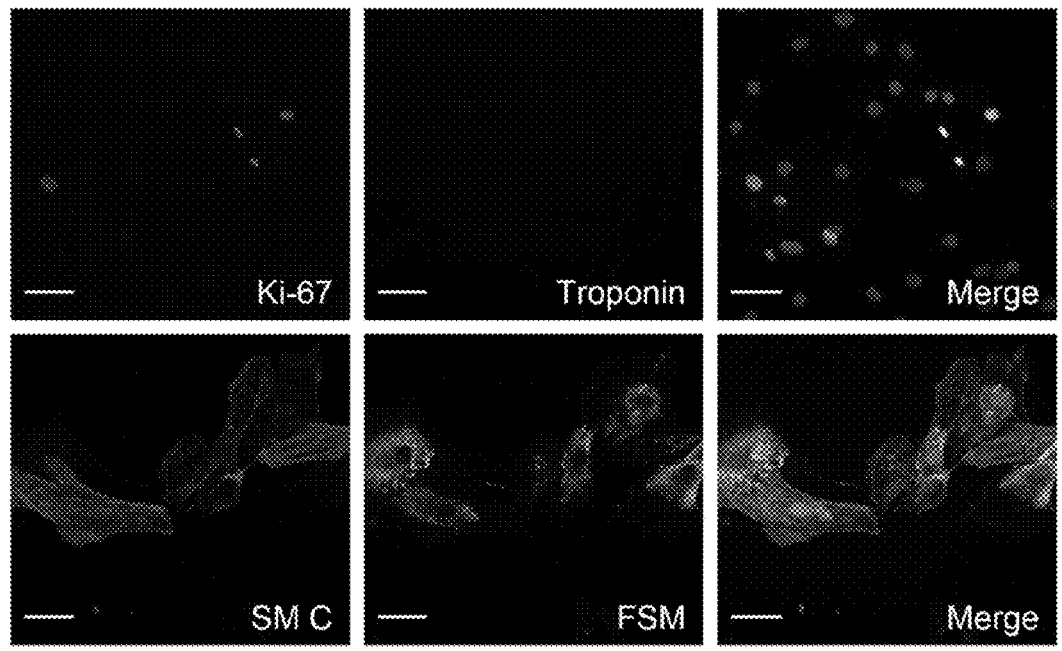
FIG. 16A is a set of florescent images of cells cultured from the left ventricle of hearts of Idiopathic Dilated Cardiomyopathy (DCM) patients immunostained with cardiac troponin T (Thermo Scientific, Catalogue Number: MS-295-P0), Ki-67 (Millipore, Catalogue Number: AB9260), smooth muscle cell actin (Biomedical Technologies Inc., Catalogue Number: BT-562), or fibroblast-specific marker (Novus Biologicals, Catalogue Number: NB100-1845).
Figure 16B:
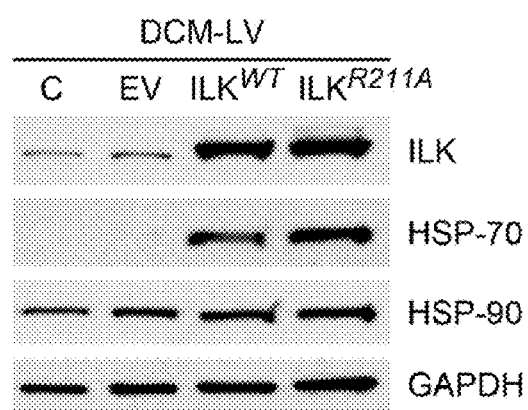
FIG. 16B is a set of Western blot images performed on cell lysates prepared as in FIG. 16A using the indicated antibodies and with GAPDH used as a loading control.

The levels of endogenous ILK gene in patients with advanced heart failure (HF) due to idiopathic dilated cardiomyopathy (DCM) were shown to be significantly reduced in both the left and right ventricles, consistent with a deficit in ILK-mediated cardiac function (FIG. 15). The effects of ILK$^{R211A}$ over-expression using adenoviral gene transduction were determined on cardiac cells derived from the LV of DCM patients. Here, cardiac cell cultures at 3 weeks were comprised mainly of cells with a cardiac fibroblast phenotype reflecting the limited capacity of adult human cardiomyocytes to survive long-lived in culture in vitro. (See FIG. 16A) As was the case transgenic heart tissue, ILK$^{R211A}$, more so than wild-type ILK, but not vector control-infected, cardiac fibroblasts derived from DCM showed specific induction of Hsp70, but not Hsp90, expression that correlated with higher ILK expression levels (See FIG. 16B). Taken together, these results suggest that mutation of wild type ILK to ILK_S343D, and especially to ILK_R211A, results in the induction of Hsp70, which in turn, serves to stabilize elevated expression levels of the client kinase.

Figure 17A:
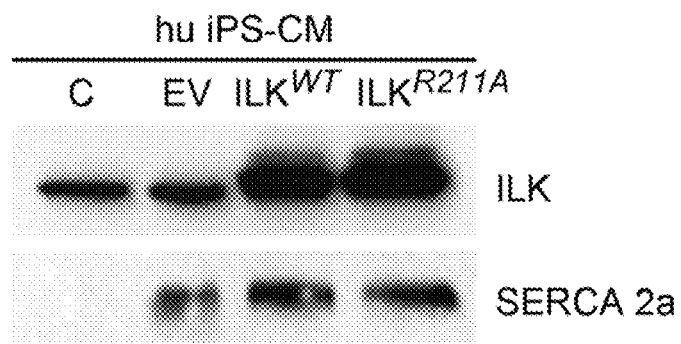
FIG. 17A is a set of images of Western blots of cell lysates of induced pluripotency stem (iPS) cells after culturing for 48 hours and infection with ILK expressing adenovirus using the antibodies directed to ILK or SERCA2 showing that ILK and ILK_R211A activate SERCA2 in human iPS-derived cardiomyocytes with human cardiomyocytes derived from induced pluripotency (iPS) stem cells purchased from Cellular Dynamics International and cultured for 10 days according to the manufacturer's protocol, and the infected with adenoviral constructs described previously containing either ILK_R211A, ILK$^{WT}$, empty vector (EV), or no treatment C.

The capacity of various ILK mutations to induce the expression of sarcoplasmic reticulum calcium ATPase isoform 2a (SERCA2) was confirmed in human cardiomyocytes derived from induced pluripotent stem (iPS) cells following infection with adenovirus expressing ILK WT, ILK$^{R211A}$, or control vector (See FIG. 17A). Human cardiomyocyte cells were identified by phase contrast imaging, green fluorescence indicating ILK expression, and red fluorescence indicating monomeric red fluorescent imaging (mRFP) under the control of the myosin heavy chain 6 (myh6) promoter (data not shown). ILK expression levels corresponded to those observed in transgenic myocardia with the highest expression in the ILK$^{R211A}$-treated cardiomyocytes despite using the same virus concentration which yielded similar (~80%) transfection efficiency. ILK is also shown to interact with SERCA2 in addition to Hsc70 by co-immunoprecipitation. (See FIG. 14B) As shown, both ILK$^{R211A}$ and ILK$^{WT}$ induced increased expression of SERCA2 protein expression in this in vitro model of human contractile cardiomyocytes.

Figure 17B:
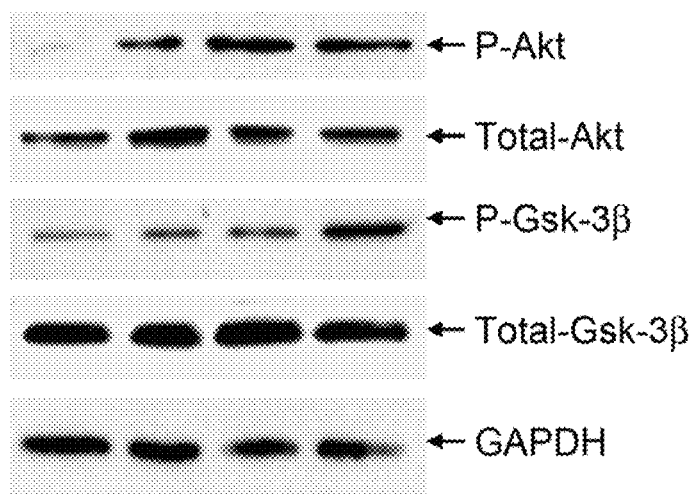
FIG. 17B is a set of images of Western blots of cell lysates of induced pluripotency stem (iPS) cells prepared as in FIG. 17A showing that ILK and ILK_R211A increase phosphorylation of protein kinase B (p-Akt/PKB) on Ser473 and glycogen synthase-3β (p-GSK-3β) on Ser9. The increase in p-GSK-3β was greater in response to ILK_R211A. GAPDH is used as a loading control.

ILK is a protein Ser/Thr kinase that causes phosphorylation of Akt/PKB on Ser473 and GSK-3β on Ser9. Conversely, the ILK$^{R211A}$ mutation is thought to be either null or inhibitory to growth-factor-stimulated canonical ILK signaling. However, we observed increased levels of phosphorylated PKB in human iPS-derived cardiomyocytes following overexpression of wild type or ILK$^{R211A}$, and levels of p-GSK-3β, a known cardioprotective target (see, e.g., Miura T et al., "GSK-3beta, a therapeutic target for cardiomyocyte protection, *Circ J* 73(7):1184-1192 (2009), the entire contents and disclosure of which is hereby incorporated by reference), that showed the highest increase in ILK$^{R211A}$ (See FIG. 17B). This indicates that ILK$^{R211A}$ may be competent for cytoprotective signaling in human cardiomyocytes as a result of stabilization by Hsc70.

The induction of Hsp70 represents a conserved protective response to heat-shock or hypoxic stress in diverse cell types and is shown experimentally to confer cardioprotection against ischemic-reperfusion injury. See, e.g., Chang W et al., "Mesenchymal stem cells pretreated with delivered Hph-1-Hsp70 protein are protected from hypoxia-mediated cell death and rescue heart functions from myocardial injury," *Stem Cells* 27(9):2283-2292 (2009); Peng W et al., "Cardioprotection by CaMKII-deltaB is mediated by phosphorylation of heat shock factor 1 and subsequent expression of inducible heat shock protein 70," *Circ Res* 106(1):102-110 (2009); and Okubo S et al., "Gene transfer of heat-shock protein 70 reduces infarct size in vivo after ischemia/reperfusion in the rabbit heart," *Circulation* 103(6):877-881 (2001), the entire contents and disclosure of which is hereby incorporated by reference. Although the molecular mechanism through which Hsp70 mediates cytoprotection is poorly understood, it is thought to depend upon the context-specific profile and fate of Hsp70 client proteins, which may be marked for stabilization or clearance. Our results in transgenic mouse hearts, human cardiomyocytes and human cardiac fibroblasts indicate that mutations in ILK elicit specific binding to Hsc70 that results in increased ILK expression levels which, in line with the degree of cardioprotection conferred, were proportionally highest with the R211A mutant protein and intermediate with the S343D mutant protein compared to that with wild-type ILK.

The increased expression levels of ILK seen with the R211A mutation correlated with increased phosphorylation of canonical ILK targets PKB and GSK-3β in transgenic mice in vivo, and in human cardiomyocytes in vitro. This finding is consistent with the capacity of Hsp chaperones, which have evolved to recognize subtle changes in molecular structure, to transduce a critical layer of regulation affecting protein expression and function. Rescue of the functional activity of disease-causing enzyme missense mutations, including mutant allelic function of the TP53 tumor suppressor gene that causes the dominant cancer susceptibility disorder, Li-Fraumeni syndrome, was recently shown to require pharmacological Hsp70 induction. However, our own data indicate that the specific kinase mutation is by itself sufficient for Hsp70 induction, which then mediates enhanced expression levels of the client kinase.

The role of Hsp70 in oncogenesis is also dependent upon the repertoire and fate of client protein substrates. For example, permutations of interactions of Hsp70 with three different proteins in tumor cell models have opposing outcomes of apoptosis, proliferation or metastasis. Accordingly, the functional effects of the Hsp70-ILK$^{R211A}$ complex predictably reflect that of ILK$^{R211A}$ rather than that of Hsc70 per se. It is likely that the protective effects of ILK$^{R211A}$ shown here are due to its increased expression and pro-survival signaling in vulnerable, border zone cardiomyocytes during post MI remodeling. This result suggests that the function of the ILK$^{R211A}$ mutation is preserved in a cell-autonomous manner: the point mutation in its PH domain renders it resistant to proximal PI3K-mediated signaling through receptor tyrosine kinase (RTK) or β1 integrin-mediated inputs, whereas the intact Ser343 locus renders it competent for substrate recruitment and signaling. An alternative explanation is that the cytoprotective effects of ILK$^{R211A}$ over-expression result from enhanced scaffolding as opposed to kinase function, in which case phosphorylation of Akt/PKB and GSK-3β may be attributable to other, not-yet-identified ILK-interacting proteins. The cardioprotective effects of ILK$^{R211A}$ observed in this study are consistent with previous studies in which cardiac-specific over-expression of ILK$^{R211A}$ did not elicit either baseline or angiotensin-II-induced hypertrophic phenotype that was seen in that of wild-type ILK, and with the absence of an adverse cardiac phenotype in ILK$^{R211A}$ knock-in mice. See, e.g., Lange A et al., "Integrin-linked kinase is an adaptor with essential functions during mouse development," Nature 461(7266):1002-1006 (2009), the entire contents and disclosure of which is hereby incorporated by reference.

Figure 18:
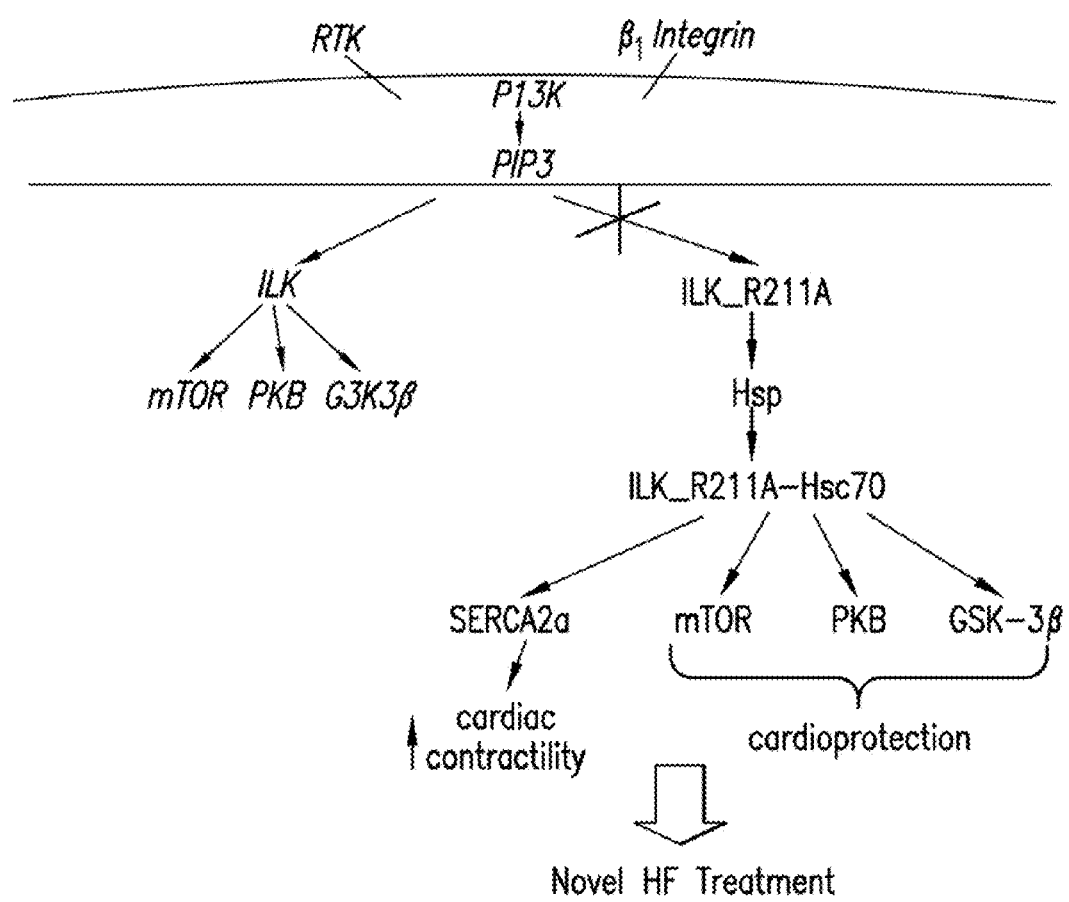
FIG. 18 is a theorized schematic showing a proposed model of cytoprotective ILK_R211A signaling in cardiac cells.

The proposed mechanism underlying the capacity of ILK$^{R211A}$ over-expression to promote enhanced cardioprotection compared to wild type ILK is modeled schematically in FIG. 18. The right side of the schema represents the newly hypothesized pathways activated by ILK$^{R211A}$, which carries a point mutation at amino acid 211 in the PH domain that impairs membrane binding and activation (denoted by 'X' in diagram). ILK$^{R211A}$ protein is herein shown to have novel and unanticipated cardioprotective effects. ILK$^{R211A}$ protein is proposed as a means to increase the expression of Hsp70, Hsc70, p-GSK-3β, and SERCA2 in cardiomyocytes, and to increase the expression of Hsp70 in cardiac fibroblasts. These responses are individually and collectively cardioprotective.

ILK$^{R211A}$ activates a robust heat-shock protein (Hsp) response at the transcriptional level, and also features specific interaction of ILK$^{R211A}$ with Hsp70 cognate protein (Hsc70) at the protein level, likely as a result of misfolding of the mutant kinase. Specific binding of ILK$^{R211A}$ with Hsc70 enhances ILK expression levels several-fold and enhances canonical ILK signaling function since the catalytic kinase domain remains intact in the ILK$^{R211A}$ mutation. ILK$^{R211A}$ also exhibits specific binding to, and consequent upregulation of a key heart failure (HF) target, sarcoplasmic reticulum ATPase 2a (SERCA2), resulting in improved SR function and cardiac contractility.

Importantly, the resistance of ILK$^{R211A}$ to aberrant receptor-mediated activation reduces the risk of potential oncogenic, off-target effects associated with ILK pathway stimulation. In other words, ILK$^{R211A}$ exhibits enhanced signaling but in a cell-autonomous manner and remains resistant to potentially oncogenic, receptor-mediated hyperactivation. Indeed, the limited available data regarding the ILK$^{R211A}$ on signal transduction and cellular proliferation in cancer cell lines point to the potential anti-oncogenic properties of this mutation. Altogether, activation of the cardioprotective signaling by ILK$^{R211A}$ identifies a novel, first-in-class target for the treatment of HF of diverse causation.

The enhanced interaction of ILK$^{R211A}$ compared to the wild type kinase with Hsc70 provides a mechanism for cardioprotection, and points to nuanced specificity of Hsp70 and ILK that may also apply more generally to Hsp-client protein interactions. As in the case of ILK, the protein Ser/Thr kinases, PKB/Akt and PKCε, exhibit both cardioprotective and oncogenic properties, highlighting the unresolved but general therapeutic paradigm in which oncogenic risk is typically inherent in cardioprotective and other regenerative medicine targets. See, e.g., Jiang Z S et al., "High molecular weight FGF-2 promotes postconditioning-like cardioprotection linked to activation of the protein kinase C isoforms Akt and p70 S6 kinase. Can J Physiol Pharmacol 87(10):798-804 (2009); Sussman M et al., "'AKT'ing lessons for stem cells: regulation of cardiac myocyte and progenitor cell proliferation, Trends Cardiovasc Med 17(7):235-240 (2007); Engelman J A et al., "Targeting PI3K signalling in cancer: opportunities, challenges and limitations," Nat Rev Cancer 9(8): 550-562 (2009); and Mukherjee S et al., "Isothiocyanates sensitize the effect of chemotherapeutic drugs via modulation of protein kinase C and telomerase in cervical cancer cells," Mol Cell Biochem 330(1-2):9-22 (2009), the entire contents and disclosure of which is hereby incorporated by reference. Thus, the potency and predicted cardioselectivity of ILK$^{R211A}$ introduces the broader theme of potentially achieving enhanced efficacy/toxicity profiles through engineered mutations in cytoprotective protein kinase targets.

Suppression of sarcoplasmic endoplasmic reticulum ATPase, isoform 2a (SERCA2) leads to impaired Ca2+ sequestration, a hallmark of reduced contractility and diastolic dysfunction characteristic of advanced HF. Reduction of SERCA2 is considered a critical marker for human HF. See, e.g., Jaski B E et al., "Calcium upregulation by percutaneous administration of gene therapy in cardiac disease (CUPID Trial), a first-in-human phase 1/2 clinical trial," J Card Fail 15(3):171-181 (2009), the entire contents and disclosure of which is hereby incorporated by reference. Sarcoplasmic reticulum (SR) function is regulated predominantly by proteins controlling $Ca^{2+}$ cycling, principally reflected in the ratio of SERCA2/PLB. See, e.g., Ogletree M L et al., "Duration of left ventricular assist device support: Effects on abnormal calcium cycling and functional recovery in the failing human heart," J Heart Lung Transplant 29(5):554-561 (2010). SERCA2 activity is known to decline in late-stage HF, and SERCA2 protein and messenger RNA levels are decreased in cardiac tissue isolated from failing hearts of patients and animals with HF. See, e.g., Hasenfuss G et al., "Relation between myocardial function and expression of sarcoplasmic reticulum Ca(2+)-ATPase in failing and non-failing human myocardium," Circ Res 75(3):434-442 (1994); and de la Bastie D et al., "Function of the sarcoplasmic reticulum and expression of its Ca2(+)-ATPase gene in pressure overload-induced cardiac hypertrophy in the rat," Circ Res 66(2):554-564 (1990), the entire contents and disclosure of which is hereby incorporated by reference. Low SERCA2 levels have been shown to correlate with the abnormally high diastolic levels of cytosolic calcium and low systolic calcium released from the SR, which are typical features of HF, and typically mark poor clinical outcomes. See, e.g., Gianni D et al., "SERCA2a in heart failure: role and therapeutic prospects," J Bioenerg Biomembr 37(6):375-380 (2005); and Studeli R et al., "Diastolic dysfunction in human cardiac allografts is related with reduced SERCA2a gene expression," Am J Transplant 6(4):775-782 (2006), the entire contents and disclosure of which is hereby incorporated by reference.

A large body of experimental evidence indicates that SERCA2 plays an important role in regulating the progression of DCM. The major functional defect and common thread in DCM is systolic dysfunction often associated with decreased myofilament Ca2+ sensitivity, validating the therapeutic strategy of modulating Ca$^{++}$-handling proteins to rescue the DCM phenotype. See, e.g., Alves M L et al., "Rescue of familial cardiomyopathies by modifications at the level of sarcomere and Ca2+ fluxes," J Mol Cell Cardiol 48(5):834-842 (2010), the entire contents and disclosure of which is hereby incorporated by reference.

Notably, the first-in-human Phase 1/2 Calcium Upregulation by Percutaneous Administration of Gene Therapy in Cardiac Disease (CUPID Trial) by delivering a recombinant AAV (AAV1/SERCA2) via percutaneous intracoronary infusion indicated positive safety and efficacy end-points, including improved echocardiographic functional indices and reduced hospitalizations. In our view, the CUPID FDA Phase II trial based on AAv9-mediated SERCA2 intracoronary therapy will be probative for the commercial potential of ILK$^{R211A}$ therapy. The CUPID trial has shown a favorable efficacy/toxicity profile, thus catalyzing the concept of "gene therapy in HF" arena. It is also likely that SERCA2 will not be curative for many HF patients since it is predicated on improving the diastolic properties of existing, viable cardiomyocytes, whereas cardiomyocyte loss is the pathological hallmark of advanced HF irrespective of etiology.

In addition to its cardioprotective and cardiomyogenic properties, ILK$^{R211A}$ is shown to have specific binding to, and causes upregulation of, the key calcium ion-cycling protein, SERCA2, the suppression of which leads to impaired Ca2+ sequestration, which is a hallmark of reduced contractility and diastolic dysfunction characteristic of advanced HF. These data provide an important finding since they implicate upregulation of SR function as a novel mechanism for ILK-mediated cardioprotection. Our findings indicate that ILK$^{R211A}$ may be potently cardioprotective through heat-shock protein- and SERCA2-based mechanisms.

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method comprising administering a composition comprising a polynucleotide directly to the heart of an individual following left anterior descending (LAD) occlusion in the individual to thereby reduce infarct size, improve stroke volume and/or decrease heart rate, wherein the polynucleotide encodes human ILK (SEQ ID NO: 1) with an amino acid substitution at amino acid residue 211 of SEQ ID NO: 1 replacing arginine (R) with alanine (A), ILKR211A wherein the ILKR211A is expressed in the heart.

2. The method of claim 1, wherein the polynucleotide is on a vector.

3. The method of claim 2, wherein the vector is introduced into the one or more cells by a retrovirus, an adenovirus, or an adeno-associated virus (AAV).

4. The method of claim 1, wherein the composition further comprises a delivery reagent.

5. The method of claim 4, wherein the delivery reagent comprises an emulsion, micelles, liposomes, microcapsules, or viral envelopes.

6. The method of claim 1, wherein the individual is having or has had heart failure, a myocardial infarction, an ischemic condition of the heart, a cardiomyopathy, a congential heart defect, a valvular heart disease, or a post-surgical cardiac dysfunction.

* * * * *

SEQUENCE LISTING

```
<160> NUMBER OF SEQ ID NOS: 10

<210> SEQ ID NO 1
<211> LENGTH: 452
<212> TYPE: PRT
<213> ORGANISM: Homo sapiens

<400> SEQUENCE: 1

Met Asp Asp Ile Phe Thr Gln Cys Arg Glu Gly Asn Ala Val Ala Val
1               5                   10                  15

Arg Leu Trp Leu Asp Asn Thr Glu Asn Asp Leu Asn Gln Gly Asp Asp
            20                  25                  30

His Gly Phe Ser Pro Leu His Trp Ala Cys Arg Glu Gly Arg Ser Ala
        35                  40                  45

Val Val Glu Met Leu Ile Met Arg Gly Ala Arg Ile Asn Val Met Asn
    50                  55                  60

Arg Gly Asp Asp Thr Pro Leu His Leu Ala Ala Ser His Gly His Arg
65                  70                  75                  80

Asp Ile Val Gln Lys Leu Leu Gln Tyr Lys Ala Asp Ile Asn Ala Val
                85                  90                  95

Asn Glu His Gly Asn Val Pro Leu His Tyr Ala Cys Phe Trp Gly Gln
            100                 105                 110

Asp Gln Val Ala Glu Asp Leu Val Ala Asn Gly Ala Leu Val Ser Ile
        115                 120                 125

Cys Asn Lys Tyr Gly Glu Met Pro Val Asp Lys Ala Lys Ala Pro Leu
    130                 135                 140

Arg Glu Leu Leu Arg Glu Arg Ala Glu Lys Met Gly Gln Asn Leu Asn
145                 150                 155                 160

Arg Ile Pro Tyr Lys Asp Thr Phe Trp Lys Gly Thr Thr Arg Thr Arg
                165                 170                 175

Pro Arg Asn Gly Thr Leu Asn Lys His Ser Gly Ile Asp Phe Lys Gln
            180                 185                 190

Leu Asn Phe Leu Thr Lys Leu Asn Glu Asn His Ser Gly Glu Leu Trp
        195                 200                 205

Lys Gly Arg Trp Gln Gly Asn Asp Ile Val Val Lys Val Leu Lys Val
    210                 215                 220

Arg Asp Trp Ser Thr Arg Lys Ser Arg Asp Phe Asn Glu Glu Cys Pro
225                 230                 235                 240

Arg Leu Arg Ile Phe Ser His Pro Asn Val Leu Pro Val Leu Gly Ala
```

-continued

```
                    245                 250                 255
Cys Gln Ser Pro Pro Ala Pro His Pro Thr Leu Ile Thr His Trp Met
                260                 265                 270

Pro Tyr Gly Ser Leu Tyr Asn Val Leu His Glu Gly Thr Asn Phe Val
            275                 280                 285

Val Asp Gln Ser Gln Ala Val Lys Phe Ala Leu Asp Met Ala Arg Gly
        290                 295                 300

Met Ala Phe Leu His Thr Leu Glu Pro Leu Ile Pro Arg His Ala Leu
305                 310                 315                 320

Asn Ser Arg Ser Val Met Ile Asp Glu Asp Met Thr Ala Arg Ile Ser
                325                 330                 335

Met Ala Asp Val Lys Phe Ser Phe Gln Cys Pro Gly Arg Met Tyr Ala
                340                 345                 350

Pro Ala Trp Val Ala Pro Glu Ala Leu Gln Lys Lys Pro Glu Asp Thr
            355                 360                 365

Asn Arg Arg Ser Ala Asp Met Trp Ser Phe Ala Val Leu Leu Trp Glu
        370                 375                 380

Leu Val Thr Arg Glu Val Pro Phe Ala Asp Leu Ser Asn Met Glu Ile
385                 390                 395                 400

Gly Met Lys Val Ala Leu Glu Gly Leu Arg Pro Thr Ile Pro Pro Gly
                405                 410                 415

Ile Ser Pro His Val Cys Lys Leu Met Lys Ile Cys Met Asn Glu Asp
                420                 425                 430

Pro Ala Lys Arg Pro Lys Phe Asp Met Ile Val Pro Ile Leu Glu Lys
            435                 440                 445

Met Gln Asp Lys
        450

<210> SEQ ID NO 2
<211> LENGTH: 452
<212> TYPE: PRT
<213> ORGANISM: Homo sapiens

<400> SEQUENCE: 2

Met Asp Asp Ile Phe Thr Gln Cys Arg Glu Gly Asn Ala Val Ala Val
1               5                   10                  15

Arg Leu Trp Leu Asp Asn Thr Glu Asn Asp Leu Asn Gln Gly Asp Asp
            20                  25                  30

His Gly Phe Ser Pro Leu His Trp Ala Cys Arg Glu Gly Arg Ser Ala
        35                  40                  45

Val Val Glu Met Leu Ile Met Arg Gly Ala Arg Ile Asn Val Met Asn
    50                  55                  60

Arg Gly Asp Asp Thr Pro Leu His Leu Ala Ala Ser His Gly His Arg
65                  70                  75                  80

Asp Ile Val Gln Lys Leu Leu Gln Tyr Lys Ala Asp Ile Asn Ala Val
                85                  90                  95

Asn Glu His Gly Asn Val Pro Leu His Tyr Ala Cys Phe Trp Gly Gln
            100                 105                 110

Asp Gln Val Ala Glu Asp Leu Val Ala Asn Gly Ala Leu Val Ser Ile
        115                 120                 125

Cys Asn Lys Tyr Gly Glu Met Pro Val Asp Lys Ala Lys Ala Pro Leu
    130                 135                 140

Arg Glu Leu Leu Arg Glu Arg Ala Glu Lys Met Gly Gln Asn Leu Asn
145                 150                 155                 160

Arg Ile Pro Tyr Lys Asp Thr Phe Trp Lys Gly Thr Thr Arg Thr Arg
```

-continued

```
                165                 170                 175
Pro Arg Asn Gly Thr Leu Asn Lys His Ser Gly Ile Asp Phe Lys Gln
        180                 185                 190

Leu Asn Phe Leu Thr Lys Leu Asn Glu Asn His Ser Gly Glu Leu Trp
        195                 200                 205

Lys Gly Ala Trp Gln Gly Asn Asp Ile Val Val Lys Val Leu Lys Val
        210                 215                 220

Arg Asp Trp Ser Thr Arg Lys Ser Arg Asp Phe Asn Glu Glu Cys Pro
225                 230                 235                 240

Arg Leu Arg Ile Phe Ser His Pro Asn Val Leu Pro Val Leu Gly Ala
                245                 250                 255

Cys Gln Ser Pro Pro Ala Pro His Pro Thr Leu Ile Thr His Trp Met
            260                 265                 270

Pro Tyr Gly Ser Leu Tyr Asn Val Leu His Glu Gly Thr Asn Phe Val
        275                 280                 285

Val Asp Gln Ser Gln Ala Val Lys Phe Ala Leu Asp Met Ala Arg Gly
        290                 295                 300

Met Ala Phe Leu His Thr Leu Glu Pro Leu Ile Pro Arg His Ala Leu
305                 310                 315                 320

Asn Ser Arg Ser Val Met Ile Asp Glu Asp Met Thr Ala Arg Ile Ser
                325                 330                 335

Met Ala Asp Val Lys Phe Ser Phe Gln Cys Pro Gly Arg Met Tyr Ala
            340                 345                 350

Pro Ala Trp Val Ala Pro Glu Ala Leu Gln Lys Lys Pro Glu Asp Thr
        355                 360                 365

Asn Arg Arg Ser Ala Asp Met Trp Ser Phe Ala Val Leu Leu Trp Glu
        370                 375                 380

Leu Val Thr Arg Glu Val Pro Phe Ala Asp Leu Ser Asn Met Glu Ile
385                 390                 395                 400

Gly Met Lys Val Ala Leu Glu Gly Leu Arg Pro Thr Ile Pro Pro Gly
                405                 410                 415

Ile Ser Pro His Val Cys Lys Leu Met Lys Ile Cys Met Asn Glu Asp
            420                 425                 430

Pro Ala Lys Arg Pro Lys Phe Asp Met Ile Val Pro Ile Leu Glu Lys
        435                 440                 445

Met Gln Asp Lys
    450

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgtgcagacc acgatgtgg                                                   19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
```
gactgaggcc cgtcatctc                                                        19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cacgatcagt atattctgag                                                       20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgtggtctgc tcggcagaag                                                       20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agggctgcca tttgcagtgg                                                       20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
catttgatgt tagtggggtc t                                                     21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cggatttggt cgtattgggc                                                       20

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctccatggtg gtgaagacg                                                        19